United States Patent
Rockweiler et al.

(10) Patent No.: US 10,434,318 B2
(45) Date of Patent: Oct. 8, 2019

(54) SYSTEMS AND METHODS FOR FACILITATING SELECTING OF ONE OR MORE VECTORS IN A MEDICAL DEVICE

(71) Applicant: Cardiac Pacemakers, Inc., St. Paul, MN (US)

(72) Inventors: Holly E. Rockweiler, San Francisco, CA (US); Sunipa Saha, Shoreview, MN (US); Keith L. Herrmann, Minneapolis, MN (US); Yinghong Yu, Shoreview, MN (US); Joel A. Krueger, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 178 days.

(21) Appl. No.: 14/574,908

(22) Filed: Dec. 18, 2014

(65) Prior Publication Data

US 2015/0165205 A1 Jun. 18, 2015

Related U.S. Application Data

(60) Provisional application No. 61/917,836, filed on Dec. 18, 2013.

(51) Int. Cl.
| | |
|---|---|
| *A61N 1/368* | (2006.01) |
| *A61N 1/365* | (2006.01) |

(Continued)

(52) U.S. Cl.
CPC ....... *A61N 1/3686* (2013.01); *A61N 1/36521* (2013.01); *A61N 1/371* (2013.01); *A61N 1/37247* (2013.01); *A61N 1/36185* (2013.01)

(58) Field of Classification Search
None
See application file for complete search history.

(56) References Cited

U.S. PATENT DOCUMENTS

| | | | |
|---|---|---|---|
| 6,128,535 A | 10/2000 | Maarse | |
| 6,192,275 B1 | 2/2001 | Zhu et al. | |

(Continued)

FOREIGN PATENT DOCUMENTS

| | | |
|---|---|---|
| CN | 101668479 A | 3/2010 |
| CN | 105828872 A | 8/2016 |

(Continued)

OTHER PUBLICATIONS

Rogers, D. P., P. D. Lambiase, M. D. Lowe and A. W. Chow. A randomized double-blind crossover trial of triventricular versus biventricular pacing in heart failure. Eur J Heart Fail 2012;14(5): 495-505.

(Continued)

*Primary Examiner* — Erica S Lee

(74) *Attorney, Agent, or Firm* — Schwegman Lundberg & Woessner, P.A.

(57) ABSTRACT

Some systems and methods may facilitate selection of a vector for delivering electrical stimulation to a patient's heart. One method may include displaying a plurality of vectors on a display screen wherein each vector represents a different combination of three or more electro-stimulation electrodes, determining an electrical impedance for each of the plurality of vectors, displaying on the display screen the electrical impedance for each of the plurality of vectors, receiving a selection of a set of the plurality of vectors, determining, for each of the vectors in the set of vectors, a capture threshold, displaying on the display screen the capture threshold for each of the vectors in the set of vectors, receiving a selection of a vector from the set of vectors for delivery of electrical stimulation to the patient's heart, and programming the electro-stimulation device electrical stimulation to the patient's heart via the selected vector.

16 Claims, 19 Drawing Sheets

(51) Int. Cl.
*A61N 1/37* (2006.01)
*A61N 1/372* (2006.01)
*A61N 1/36* (2006.01)

(56) References Cited

U.S. PATENT DOCUMENTS

| | | | |
|---|---|---|---|
| 6,226,551 B1 | 5/2001 | Zhu et al. |
| 6,421,564 B1 | 7/2002 | Yerich et al. |
| 6,463,327 B1 | 10/2002 | Lurie et al. |
| 6,493,586 B1 | 12/2002 | Stahmann et al. |
| 6,587,726 B2 | 7/2003 | Lurie et al. |
| 6,615,089 B1 | 9/2003 | Russie et al. |
| 6,772,008 B2 | 8/2004 | Zhu et al. |
| 6,922,589 B2 | 7/2005 | Stahmann et al. |
| 6,937,901 B2 | 8/2005 | Zhu et al. |
| 6,978,178 B2 | 12/2005 | Sommer et al. |
| 7,031,773 B1 | 4/2006 | Levine et al. |
| 7,123,963 B2 | 10/2006 | Sawchuk et al. |
| 7,200,439 B2 | 4/2007 | Zdeblick et al. |
| 7,225,016 B1 | 5/2007 | Koh |
| 7,225,035 B2 | 5/2007 | Brabec et al. |
| 7,228,174 B2 | 6/2007 | Burnes et al. |
| 7,277,757 B2 | 10/2007 | Casavant et al. |
| 7,299,093 B2 | 11/2007 | Zhu et al. |
| 7,328,067 B2 | 2/2008 | Zhu et al. |
| 7,340,302 B1 | 3/2008 | Falkenberg et al. |
| 7,363,086 B1 | 4/2008 | Koh et al. |
| 7,392,086 B2 | 6/2008 | Sathaye |
| 7,412,287 B2 | 8/2008 | Yonce et al. |
| 7,469,161 B1 | 12/2008 | Gandhi et al. |
| 7,471,983 B2 | 12/2008 | Voegele et al. |
| 7,496,409 B2 | 2/2009 | Greenhut et al. |
| 7,509,170 B2 | 3/2009 | Zhang et al. |
| 7,555,336 B2 | 6/2009 | Sheth et al. |
| 7,555,340 B2 | 6/2009 | Dong et al. |
| 7,587,240 B2 | 9/2009 | Zhang et al. |
| 7,620,452 B1 | 11/2009 | Russie |
| 7,657,314 B2 | 2/2010 | Sathaye et al. |
| 7,680,536 B2 | 3/2010 | Sathaye et al. |
| 7,711,423 B2 | 5/2010 | Burnes et al. |
| 7,734,333 B2 | 6/2010 | Ghanem et al. |
| 7,738,959 B2 | 6/2010 | Manrodt et al. |
| 7,761,164 B2 | 7/2010 | Verhoef et al. |
| 7,792,585 B1 | 9/2010 | Shelchuk |
| 7,848,812 B2 | 12/2010 | Crowley et al. |
| 7,953,489 B2 | 5/2011 | Warren et al. |
| 7,957,803 B2 | 6/2011 | Zhang et al. |
| 7,996,072 B2 | 8/2011 | Haefner |
| 8,010,203 B2 | 8/2011 | DeMulling et al. |
| 8,014,860 B2 | 9/2011 | Kwok et al. |
| 8,036,743 B2 | 10/2011 | Savage et al. |
| 8,065,002 B2 | 11/2011 | Arand et al. |
| 8,078,276 B2 | 12/2011 | Dong et al. |
| 8,135,463 B2 | 3/2012 | Burnes et al. |
| 8,145,311 B2 | 3/2012 | Min |
| 8,150,512 B2 | 4/2012 | Bornzin et al. |
| 8,160,700 B1 | 4/2012 | Ryu et al. |
| 8,175,703 B2 | 5/2012 | Dong et al. |
| 8,185,202 B2 | 5/2012 | Sathaye |
| 8,200,331 B2 | 6/2012 | Libbus et al. |
| 8,200,332 B2 | 6/2012 | Libbus et al. |
| 8,209,010 B2 | 6/2012 | Ryu et al. |
| 8,209,013 B2 | 6/2012 | Brooke et al. |
| 8,233,979 B1 | 7/2012 | Shelchuk |
| 8,255,048 B2 | 8/2012 | Dal Molin et al. |
| 8,260,421 B2 | 9/2012 | Sathaye |
| 8,265,736 B2 | 9/2012 | Sathaye et al. |
| 8,265,755 B2 | 9/2012 | Min |
| 8,265,759 B2 | 9/2012 | Tehrani et al. |
| 8,271,086 B2 | 9/2012 | Voegele et al. |
| 8,271,087 B2 | 9/2012 | Sathaye et al. |
| 8,285,377 B2 | 10/2012 | Rosenberg et al. |
| 8,301,246 B2 | 10/2012 | Park et al. |
| 8,306,622 B2 | 11/2012 | Arcot-Krishnamurthy et al. |
| 8,326,418 B2 | 12/2012 | Sommer et al. |
| 8,326,419 B2 | 12/2012 | Rosenberg et al. |
| 8,335,565 B2 | 12/2012 | Freeberg et al. |
| 8,346,372 B2 | 1/2013 | Yang et al. |
| 8,401,646 B2 | 3/2013 | Stadler et al. |
| 8,447,400 B2 | 5/2013 | More et al. |
| 8,744,572 B1 | 6/2014 | Greenhut et al. |
| 2004/0220636 A1* | 11/2004 | Burnes ............... A61N 1/36521 607/17 |
| 2006/0155202 A1 | 7/2006 | Arand et al. |
| 2007/0129764 A1 | 6/2007 | Burnes |
| 2007/0276445 A1 | 11/2007 | Sanghera et al. |
| 2008/0059492 A1* | 3/2008 | Tarin ................ G06F 17/30315 |
| 2008/0077186 A1 | 3/2008 | Thompson et al. |
| 2009/0043351 A1 | 2/2009 | Sathaye et al. |
| 2009/0043352 A1 | 2/2009 | Brooke et al. |
| 2009/0054946 A1 | 2/2009 | Sommer et al. |
| 2009/0210024 A1 | 8/2009 | M. |
| 2010/0125306 A1 | 5/2010 | McCabe et al. |
| 2010/0152801 A1 | 6/2010 | Koh et al. |
| 2010/0198292 A1 | 8/2010 | Honeck et al. |
| 2010/0305637 A1 | 12/2010 | McCabe et al. |
| 2010/0305638 A1 | 12/2010 | McCabe et al. |
| 2010/0305647 A1 | 12/2010 | McCabe et al. |
| 2010/0324617 A1 | 12/2010 | Ong |
| 2011/0004264 A1 | 1/2011 | Siejko et al. |
| 2011/0022110 A1 | 1/2011 | Min |
| 2011/0022112 A1 | 1/2011 | Min |
| 2011/0098770 A1 | 4/2011 | Ryu et al. |
| 2011/0098773 A1 | 4/2011 | Brisben et al. |
| 2011/0098774 A1 | 4/2011 | Brisben et al. |
| 2011/0106213 A1 | 5/2011 | Davis et al. |
| 2011/0152956 A1 | 6/2011 | Hincapie Ordonez et al. |
| 2011/0196441 A1 | 8/2011 | Ryu et al. |
| 2011/0196442 A1 | 8/2011 | Ryu et al. |
| 2011/0245890 A1 | 10/2011 | Brisben et al. |
| 2011/0319954 A1 | 12/2011 | Niazi et al. |
| 2012/0035685 A1 | 2/2012 | Saha et al. |
| 2012/0078320 A1* | 3/2012 | Schotzko ............... A61N 1/368 607/17 |
| 2012/0101543 A1 | 4/2012 | Demmer et al. |
| 2012/0101546 A1 | 4/2012 | Stadler et al. |
| 2012/0130442 A1 | 5/2012 | Rockweiler et al. |
| 2012/0150253 A1 | 6/2012 | Burnes et al. |
| 2012/0185012 A1 | 7/2012 | Ryu et al. |
| 2012/0185013 A1 | 7/2012 | Sivard et al. |
| 2012/0191154 A1 | 7/2012 | Ryu et al. |
| 2012/0229496 A1 | 9/2012 | Bloemer |
| 2012/0253359 A1 | 10/2012 | Koh et al. |
| 2012/0271371 A1 | 10/2012 | Keel et al. |
| 2012/0290036 A1 | 11/2012 | Karamanoglu et al. |
| 2012/0296387 A1 | 11/2012 | Zhang et al. |
| 2012/0296388 A1 | 11/2012 | Zhang et al. |
| 2012/0323291 A1 | 12/2012 | Sathaye et al. |
| 2012/0330372 A1 | 12/2012 | Sathaye et al. |
| 2013/0006332 A1 | 1/2013 | Sommer et al. |
| 2013/0030487 A1 | 1/2013 | Keel et al. |
| 2013/0035737 A1 | 2/2013 | Ryu et al. |
| 2013/0035738 A1 | 2/2013 | Karst et al. |
| 2013/0046356 A1 | 2/2013 | Jensen et al. |
| 2013/0046369 A1 | 2/2013 | Eggen et al. |
| 2013/0053916 A1 | 2/2013 | Sambelashvili et al. |
| 2013/0053918 A1 | 2/2013 | Sambelashvili et al. |
| 2013/0183182 A1 | 7/2013 | White, Jr. |
| 2013/0261473 A1 | 10/2013 | Xi et al. |
| 2013/0261687 A1 | 10/2013 | Xi et al. |
| 2013/0289640 A1* | 10/2013 | Zhang ............... A61N 1/36578 607/17 |
| 2014/0350623 A1* | 11/2014 | Fischer ................ A61N 1/3962 607/11 |
| 2015/0119950 A1* | 4/2015 | Demmer ............ A61N 1/36114 607/28 |

FOREIGN PATENT DOCUMENTS

| | | |
|---|---|---|
| JP | 2012531288 A | 2/2012 |
| JP | 2017501797 A | 1/2017 |
| WO | 2011002671 A1 | 1/2011 |
| WO | 2012019036 A1 | 2/2012 |

(56) References Cited

FOREIGN PATENT DOCUMENTS

| WO | WO-2012091848 A3 | 7/2012 |
|---|---|---|
| WO | WO-2015095581 A1 | 6/2015 |
| WO | WO-2015095581 A9 | 6/2015 |

OTHER PUBLICATIONS

Ginks, M. R., S. G. Duckett, S. Kapetanakis, J. Bostock, S. Hamid, A. Shetty, Y. Ma, K. S. Rhode, G. S. Carr-White, R. S. Razavi and C. A. Rinaldi. Multi-site left ventricular pacing as a potential treatment for patients with postero-lateral scar: insights from cardiac magnetic resonance imaging and invasive haemodynamic assessment. Europace 2012;14(3): 373-379.

Niazi, I., J. Kiemen, P. Yong, M. Newman, J. Ding, M. Stucky, S. Arcot-Krishnamurthy and N. Yu. Hemodynamic superiority of dual-site left ventricular stimulation over conventional biventricular stimulation in heart failure patients. Journal of Innovations in Cardiac Rhythm Management 2011;2(8):412-418.

Leclercq, C., F. Gadler, W. Kranig, S. Ellery, D. Gras, A. Lazarus, J. Clementy, E. Boulogne and J. C. Daubert. A randomized comparison of triple-site versus dual-site ventricular stimulation in patients with congestive heart failure. J Am Coll Cardiol 2008;51(15): 1455-1462.

Pappone, C., S. Rosanio, G. Oreto, M. Tocchi, S. Gulletta, A. Salvati, C. Dicandia, V. Santinelli, P. Mazzone, F. Veglia, J. Ding, L. Sallusti, J. Spinelli and G. Viced Vicedomini. Cardiac pacing in heart failure patients with left bundle branch block: impact of pacing site for optimizing left ventricular resynchronization. 2000;Ital Heart J 1(7): 464-469.

Medtronic, VIVA™ / VIVA™ QUAD, BRAVA™ / BRAVA™ QUAD CRT-D. Family of digital implantable cardioverter defibrillators with cardiac resynchronization therapy. Reference Manual, 2012. 418 Pgs.

St. Jude Medical 2013 Investor Conference. Power Point Slideshow. Feb. 1, 2013.

Mike Coyle, Medtronic. Executive Vice President & Cardiac and Vascular group President Medtronic Inc. Medtronic 2012 Investor Conference. Power Point Slideshow. Jun. 1, 2012. New York City.

Business Wire, Press Release. "St. Jude Medical, Inc. announced first enrollment of its MultiPoint" St. Paul, Minnesota. May 2, 2013.

"International Application Serial No. PCT/US2014/071253, International Preliminary Report on Patentability dated Jun. 30, 2016", 6 pgs.

"International Application Serial No. PCT/US2014/071253, International Search Report dated Mar. 27, 2015", 4 pgs.

"International Application Serial No. PCT/US2014/071253, Written Opinion dated Mar. 27, 2015", 4 pgs.

"Chinese Application Serial No. 201480068339.3, Office Action dated Apr. 26, 2017", w/ English Translation, 21 pgs.

"Chinese Application Serial No. 201480068339.3, Response filed Aug. 18, 2017 to Office Action dated Apr. 26, 2017", w/claims in English, 13 pgs.

"European Application Serial No. 14824726.5, Response filed Feb. 7, 2017 to Communication Pursuant to Rules 161(1) and 162 EPC dated Jul. 29, 2016", 6 pgs.

"Japanese Application Serial No. 2016-541082, Office Action dated May 16, 2017", with English translation, 10 pgs.

"Japanese Application Serial No. 2016-541082, Office Action dated Nov. 7, 2017", W/ English Translation, 4 pgs.

"Japanese Application Serial No. 2016-541082, Response filed Aug. 10, 2017 to Office Action dated May 16, 2017", w/ claims in English, 10 pgs.

* cited by examiner

SYSTEMS AND METHODS FOR FACILITATING SELECTING OF ONE OR MORE VECTORS IN A MEDICAL DEVICE

CROSS-REFERENCE TO RELATED APPLICATIONS

This application claims priority under 35 U.S.C. § 119 to U.S. Provisional Application Ser. No. 61/917,836, filed Dec. 18, 2013, the entirety of which is incorporated herein by reference.

TECHNICAL FIELD

The present disclosure generally relates to systems and methods for configuring an implantable medical device, and more specifically for assessing and selecting one or more vectors for delivery of electrical stimulation to a patient by the implantable medical device.

BACKGROUND

Cardiac rhythm management devices can include implantable or ambulatory devices, such as pacemakers, cardioverter defibrillators, or devices that can monitor one or more physiological parameters, and/or provide one or a combination of pacing, defibrillation, and cardiac resynchronization therapies. Such devices can be configured for use with a plurality of implanted or external electrodes, such as to detect or treat cardiac conditions. These electrodes may be configured in a plurality of different combinations for sensing cardiac electrical activity or delivering electrical stimulation therapy. Using different combinations of electrodes for sensing cardiac electrical activity may produce different sensed signals. Using different combinations of electrodes for delivering electrical stimulation therapy may result in different effectiveness of the therapy. Each of these electrode configurations may be termed "vectors." Selecting a proper vector for sensing cardiac electrical activity and/or for delivering electrical stimulation therapy can help ensure more effective treatment. However, in some systems, the number of available vectors is large due to the number of implanted electrodes. In such systems, assessing each vector in order to select one or more vectors for sensing and delivering electrical stimulation therapy may be time consuming, and in some cases bothersome to the patient.

SUMMARY

The present disclosure relates generally to systems and methods for assessing a plurality of vectors in an implantable medical device system, and in some cases, selecting one or more of the vectors based on the assessment for delivery of electrical stimulation therapy. In some cases, the present disclosure provides systems and methods for efficiently identifying suitable vectors for sensing cardiac electrical data and/or delivering electrical stimulation therapy. Reducing the amount of time required to identifying suitable vectors can help reduce procedure time for implanting and/or configuring an implantable medical device, and in some cases, can help reduce discomfort to the patient.

In one example, a method of facilitating selection of a vector for delivering electrical stimulation to a patient's heart via an electro-stimulation device having three or more electro-stimulation electrodes includes displaying a plurality of vectors on a display screen, wherein each vector represents a different combination of the three or more electro-stimulation electrodes, determining an electrical impedance for each of the plurality of vectors, displaying on the display screen the determined electrical impedance for each of the plurality of vectors, receiving a selection of a set of the plurality of vectors, determining, for each of the vectors in the set of the plurality of vectors, a capture threshold, displaying on the display screen the capture threshold for each of the vectors in the set of the plurality of vectors, receiving a selection of a vector from the set of the plurality of vectors for delivery of electrical stimulation to the patient's heart, and programming the electro-stimulation device to use the selected vector when delivering electrical stimulation to the patient's heart.

In another example, a system for facilitating selection of at least one vector for delivering electrical stimulation to a chamber of a patient's heart includes a pulse generator configured to deliver electrical stimulation pulses to the patient's heart, a display screen, and a controller coupled to the display screen and the pulse generator. The controller may be configured to present, at the display screen, a plurality of vectors, determine an electrical delay for the plurality of vectors, determine an impedance for the plurality of vectors, then present at the display screen the determined electrical delay and the determined impedance for each of the plurality of vectors, receive a selection of a set of vectors from the plurality of vectors, and determine, for each of the vectors in the set of vectors, a capture threshold.

In yet another example, a method of facilitating selection of at least one vector for delivering electrical stimulation to a chamber of a patient's heart includes displaying a table on a display screen, wherein the table includes a plurality of vectors represented in a corresponding plurality of rows, the table also including a plurality of columns each for displaying a corresponding one of a plurality of metrics for the corresponding vector, determining a first metric for each of the plurality of vectors, and displaying the determined first metric for each of the plurality of vectors in a first column of the table, receiving a selection of one or more of the plurality of vectors, after receiving the selection, determining a second metric for each of the one or more selected vectors while not determining the second metric for the non-selected vectors, displaying the determined second metric for each of the selected vectors in a second column of the table, and receiving a selection of one of the selected vectors for delivery of electrical stimulation to the patient's heart, resulting in a stimulation vector.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
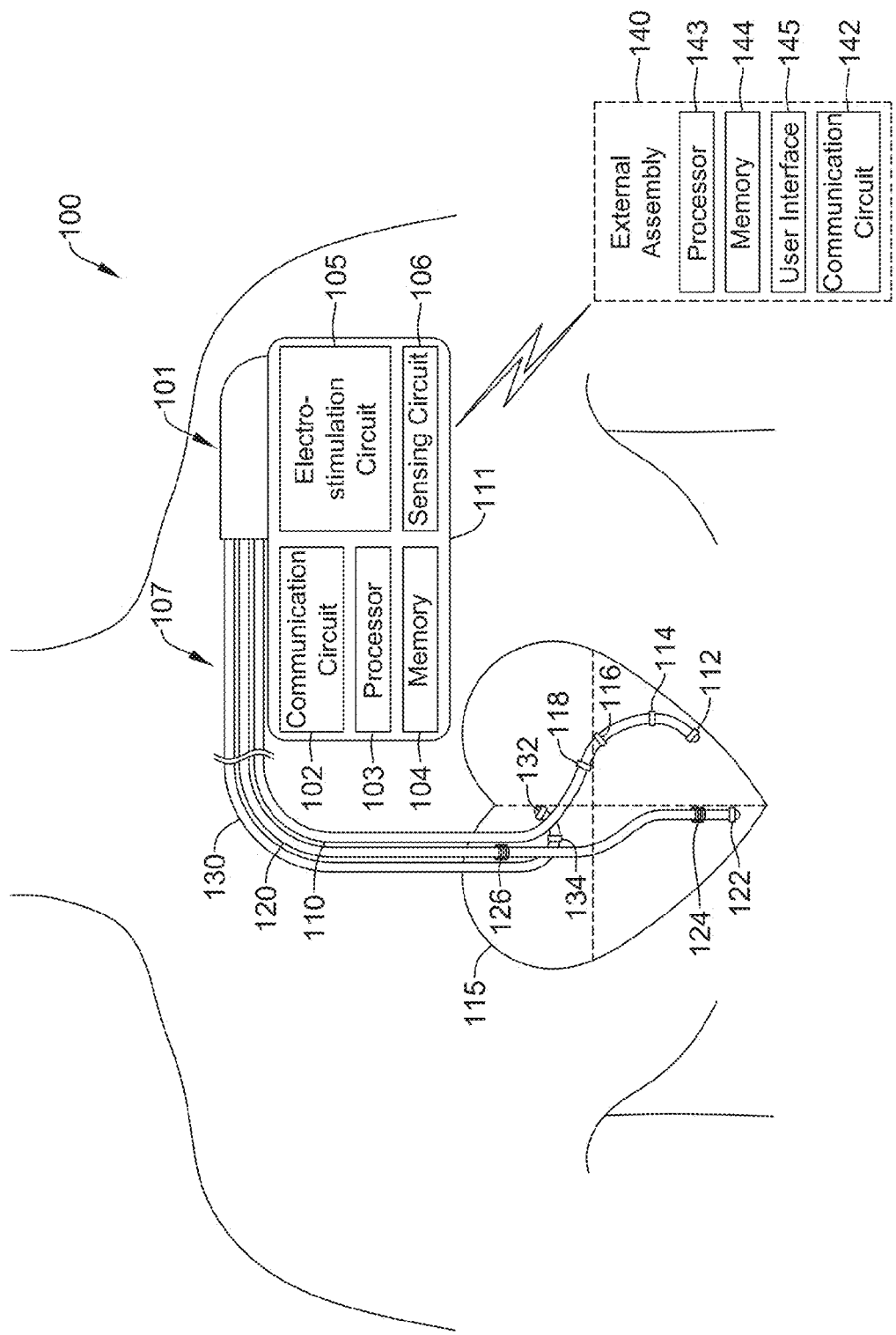
FIG. 1 is a schematic view of an illustrative implantable medical system.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer conduct intrinsic electrical stimulation signals. In other examples, diseased tissue may not conduct the intrinsic signals as quickly as healthy tissue, thereby de-synchronizing the contraction of the heart. For example, portions of the heart muscle may contract earlier or later than other muscle cells of the heart due to the different conductivity of the heart tissue with respect to the intrinsic electrical signals. This un-coordinated contraction can result in a decrease in the flow of blood throughout the rest of the body, causing various health problems.

A number of implantable medical device (IMD) systems have been developed to assist such diseased hearts. These IMD systems may include electrodes implanted on or within the heart of the patient. The IMD systems may deliver electrical stimulation therapy to the heart through these electrodes. The delivered electrical stimulation therapy may replace or assist the intrinsically generated electrical signals in causing the contraction of the heart. One type of electrical stimulation therapy is termed cardiac resynchronization therapy (CRT). In general, CRT includes delivering electrical stimulation pulses or therapy to a heart, sometimes referred to as "pacing" and "pacing pulses," in order to ensure that all portions of the heart contract in a normal, synchronous manner.

Some IMD systems for delivering CRT include multiple electrodes. However, these IMD systems may only use a portion of these electrodes for sensing cardiac electrical signals or for delivering electrical stimulation therapy at any given time. For example, some IMD systems may use a configuration of two electrodes, which may be termed a "vector," in delivering electrical stimulation therapy, with one electrode acting as a cathode and one electrode acting as an anode. Accordingly, each IMD system generally has numerous potential vectors via which the IMD system may sense cardiac electrical activity or deliver electrical stimulation therapy. However, not all of these vectors may be suitable for sensing cardiac electrical activity or delivering electrical stimulation therapy. Additionally, even of the suitable vectors, certain vectors may be more desirable than others.

Many physiological and physical factors can affect which vectors in an IMD system implanted in a given heart will be suitable or more desirable for sensing cardiac electrical activity or delivering electrical stimulation therapy to the heart. For example, such physiological and physical factors may affect the impedance, capture threshold, phrenic nerve stimulation, and electrical delay of each particular vector. Vectors with relatively low impedance are generally more desirable than vectors with relatively higher impedances. Vectors with relatively higher impedances require more power to be delivered via the vector to produce equivalent electrical stimulation relative to vectors with lower impedances. Similarly, vectors with lower capture thresholds are generally more desirable than vectors with higher capture thresholds. Capture thresholds are measures of a minimum voltage of the delivered electrical stimulation needed in order to capture the heart, which causes the heart to contract in response to the electrical stimulation. Vectors with relatively lower capture thresholds generally require less power over time to deliver effective electrical stimulation therapy for therapy than vectors with relatively higher capture thresholds. As many IMD systems are not easily accessible for battery replacement or recharging, power consumption can be an important design consideration. Phrenic nerve stimulation is another parameter to determine suitability or desirability of vectors for delivering electrical stimulation. A presence of phrenic nerve stimulation indicates that delivering electrical stimulation via the vector results in stimulation of a patient's phrenic nerve, which can be uncomfortable for a patient. Electrical delay is another parameter useful in assessing suitability or desirability of a vector. For example, vectors with longer electrical delay may be more desirable for delivering electrical stimulation therapy to the heart because delivering electrical stimulation via vectors with relatively longer electrical delays may help produce a more synchronous cardiac contraction.

Whether at the time of implantation into a patient or during follow-up visits, it is often desirable to determine the suitability of vectors of an IMD system for sensing cardiac electrical activity or delivering electrical stimulation therapy. However, IMD systems with multiple electrodes have numerous available vectors through which the IMD system could sense cardiac electrical activity and/or deliver electrical stimulation therapy. Because of the numerous potential vectors, and because determining each of the aforementioned parameters takes time, assessing all potential vectors can take an extended period of time. This can cause a strain on the patient and can consume limited hospital and physician resources. Accordingly, this disclosure describes systems and techniques for reducing the amount of time to assess vectors and find suitable or desirable vectors for sensing cardiac electrical activity and/or delivering electrical stimulation therapy in an IMD system.

FIG. 1 is a schematic view of an illustrative implantable medical system. FIG. 1 illustrates generally an example of a system 100 that can include an implantable medical device 101. Implantable medical device 101 can be coupled to one or more electro-stimulation electrodes, which can be carried by one or more implantable leads, such as implantable leads 110, 120, and 130. Implantable leads 110, 120, and 130 can be configured to receive or sense cardiac electrical signals from heart 115. In some cases, implantable medical device 101 can include a hermetically-sealed or similar housing 111. Housing 111 can include titanium or another biocompatible material, such as one or more other conductive materials.

In some instances, the electro-stimulation electrodes may be provided by a leadless cardiac pacemaker (LCP), which is in communication with other LCP's and/or with another implantable medical device 101. The use of LCP may reduce or eliminate the need for one or more of the implantable leads 110, 120 and 130, as desired.

Generally, implantable medical device 101 may include an electro-stimulation or pulse generator device. Accordingly, in some examples, implantable medical device 101 may include one or more of a pacemaker, a defibrillator, an implantable monitor, a drug delivery device, a cardiac resynchronization therapy (CRT) device, a neural stimulation device, and/or one or more other implantable assemblies configured to monitor a person or configured to provide one or more treatments to the person. Examples of such monitoring or treatment can include delivering electrical stimulation therapy to tissues such as cardiac tissue, or electrical monitoring of muscular or cardiac activity. In one example, implantable medical device 101 can include an external medical device, such as a pacing system analyzer, programmer recorder monitor, or other external medical device that can be used to configure a system of multipolar implantable leads. In some cases, implantable medical device 101 may include a subcutaneous Implantable Cardioverter-Defibrillator (S-ICD) and/or a subcutaneous pacemaker.

In the example of FIG. 1, implantable medical device 101 can be coupled to heart 115, or other body tissue, such as via electrode system 107, epicardial electrodes, or external (e.g., skin-patch) electrodes. In the system of FIG. 1, electrode system 107 includes at least one lead and at least one electro-stimulation electrode for each lead. FIG. 1 shows an example in which there are three implantable leads 110, 120, and 130. In the example of FIG. 1, implantable lead 110 can be configured for use in association with a left ventricle of heart 115. For example, implantable lead 110 can be sized and shaped to allow insertion into a coronary sinus and intravascular advancement such as to put at least one electro-stimulation electrode in association with the left ventricle of heart 115. Implantable lead 110 can be a multipolar lead, including a plurality of electro-stimulation electrodes and corresponding conductors. In an example, implantable lead 110 can include four discrete electro-stimulation electrodes, such as: tip electrode 112, first ring electrode 114, second ring electrode 116, and third ring electrode 118. In an example, electro-stimulation electrodes 114, 116, and 118 can be located near a distal portion of implantable lead 110. Each of electro-stimulation electrodes 114, 116, and 118 can be separated by electrically insulating material, thus electrically isolating the individual electro-stimulation electrodes. Each of the four left ventricular electro-stimulation electrodes 112, 114, 116, and 118 can correspond to a unique electrical conductor and can be individually addressable by sensing circuit 106 or electro-stimulation circuit 105 contained within implantable medical device 101.

In the example shown in FIG. 1, implantable lead 120 can include tip electrode 122, first coil electrode 124, and second coil electrode 126. As generally shown in FIG. 1, implantable lead 120 can, in one example, be inserted into the right atrium and right ventricle of heart 115 so that first coil electrode 124 is positioned in the right ventricle and second coil electrode 126 is positioned in the right atrium. Likewise, in the example of FIG. 1, implantable lead 130 can include tip electrode 132 and ring electrode 134. As generally shown in FIG. 1, implantable lead 130 can be configured for insertion into the right atrium of heart 115.

The physical illustration of implantable leads 110, 120, and 130 provided in FIG. 1 is an illustrative non-limiting example only. Other systems may include leads positioned differently with respect to heart 115. Additionally, other systems may have differing numbers of electro-stimulation electrodes, and the positioning of the electro-stimulation electrodes on the leads may differ. Other systems may also include more or less implantable leads. In a system that uses strictly LCPs, no leads may be required or even desired. In general, the systems and techniques of the present disclosure are amenable to any system including a plurality of electrodes that are configurable into a plurality of vectors, regardless of specific implant locations or electrode placement or numbers.

In one example, implantable medical device 101 can include a communication circuit 102, processor circuit 103, memory circuit 104, electro-stimulation circuit 105, and sensing circuit 106. Processor circuit 103 and memory circuit 104 can be used to control the operation of implantable medical device 101. For example, processor circuit 103 can be configured to detect a cardiac condition, such as by using the sensing circuit 106 or another physiological sensor, and to respond to the detected cardiac condition, such as by causing electro-stimulation circuit 105 to deliver electrical stimulation to heart 115 via one or more electrodes. Memory circuit 104 can include one or more parameters, such as for various pacing and sensing modes, test procedures or the like. Memory circuit 104 can be configured to store physiological data, such as data concerning the condition of heart 115. Memory circuit 104 can also be configured to store device data, such as data about a status of a test or a test result. In one example, implantable medical device 101 can use electro-stimulation circuit 105 or sensing circuit 106 to interface with electrode system 107. Electro-stimulation circuit 105 or sensing circuit 106 can be configured to generate an electro-stimulation signal to provide electrical stimulation therapy to heart 115, for example by using energy stored in a battery (not shown) that is stored within implantable medical device 101. Electro-stimulation circuit 105 or sensing circuit 106 can be electrically coupled to electrode system 107. For example, electrical stimulation can be transmitted from electro-stimulation circuit 105 to heart 115 via electrode system 107. Likewise, sensing circuit 106 may receive signals from electrode system 107. Communication circuit 102 can be configured to establish a data communication link between implantable medical device 101 and, for example, external assembly 140.

In some instances, implantable medical device 101 can be configured to perform vector assessments. For example, processor circuit 103 can cause electro-stimulation circuit 105 to deliver electrical stimulation via some or all of the vectors created by pairs of electro-stimulation electrodes connected to implantable leads 110, 120, and 130. Sensing circuit 106 may detect various parameters during the vector assessment and store the detected parameters in memory circuit 104. In some cases, processor circuit 103 may communicate the detected parameters to external assembly 140, via communication circuit 102. Additionally, external assembly 140 may be configured to receive detected parameters and display them with user interface 145.

Implantable medical device 101 can be configured to communicate (wired or wirelessly) via communication circuit 102 with a local or remote external device, such as external assembly 140. This can include using an RF, optical, acoustic, conductive, or other communication link. External assembly 140 can be a portion or part of a patient management system. In one example, external assembly 140 can communicate with one or more remote clients, such as web-based clients, or can be communicatively coupled to one or more servers, which can include medical and patient databases.

In some cases, external assembly 140 can include communication circuit 142, processor circuit 143, memory circuit 144, or user interface 145. In one example, communication circuit 142 can include inductive coils or radio frequency telemetry circuitry, and can be configured to communicate with implantable medical device 101. Processor circuit 143 and memory circuit 144 can be used to interpret information received from user interface 145, or can be used to determine when to use communication circuit 142 to exchange information with implantable medical device 101. In one example, processor circuit 143 and memory circuit 144 can be used to initiate a vector assessment controlled at least in part by external assembly 140 using electrode system 107. External assembly 140 can be used to perform vector assessments using electrode system 107 and can be configured to display results such as by user interface 145. In some cases, external assembly 140 is not used and it is implantable medical device 101 that is configured to perform vector assessments using electrode system 107

When used, external assembly 140 can be an adjunct (e.g., non-implantable) external assembly. In one example, external assembly 140 can include the features of implantable medical device 101 described above and below, such that external assembly 140 can be configured to be directly or indirectly coupled to the electrode system 107. For example, external assembly 140 can be configured to assess each of the potential vectors resulting from all the various combinations of electro-stimulation electrodes 112, 114, 116, 118, 122, 124, 126, 132, and 134. External assembly 140 may be able to perform an assessment by utilizing a power source (not shown) to deliver electrical stimulation pulses to electrode system 107. External assembly 140 may be equipped with one or more algorithms that automatically select one or more of the assessed vectors and configures implantable medical device 101 with the selected vectors. In other examples, a user, such as a physician or other medical professional, may view results of the assessment and provide selections of one or more vectors. These selected vectors may be communicated to implantable medical device 101 via communication circuit 142. By using external assembly 140 to perform vector assessments, implantable medical device 101 may conserve power.

User interface 145 of external assembly 140 can include, but is not limited to, a keyboard, a mouse, a light pen, a touch-screen, a display screen, a printer, or an audio speaker. In one example, user interface 145 can be configured as a full color, high definition graphical display, such as using an LCD computer monitor. In another example, user interface 145 can be configured for use as a monochromatic display, such as using a CRT monitor to display text. In some examples, user interface 145 can be configured to interactively present a graphical representation of vector assessments to a user. In other examples, user interface 145 can be configured to interactively present a text-based representation of vector assessments.

Figure 2:
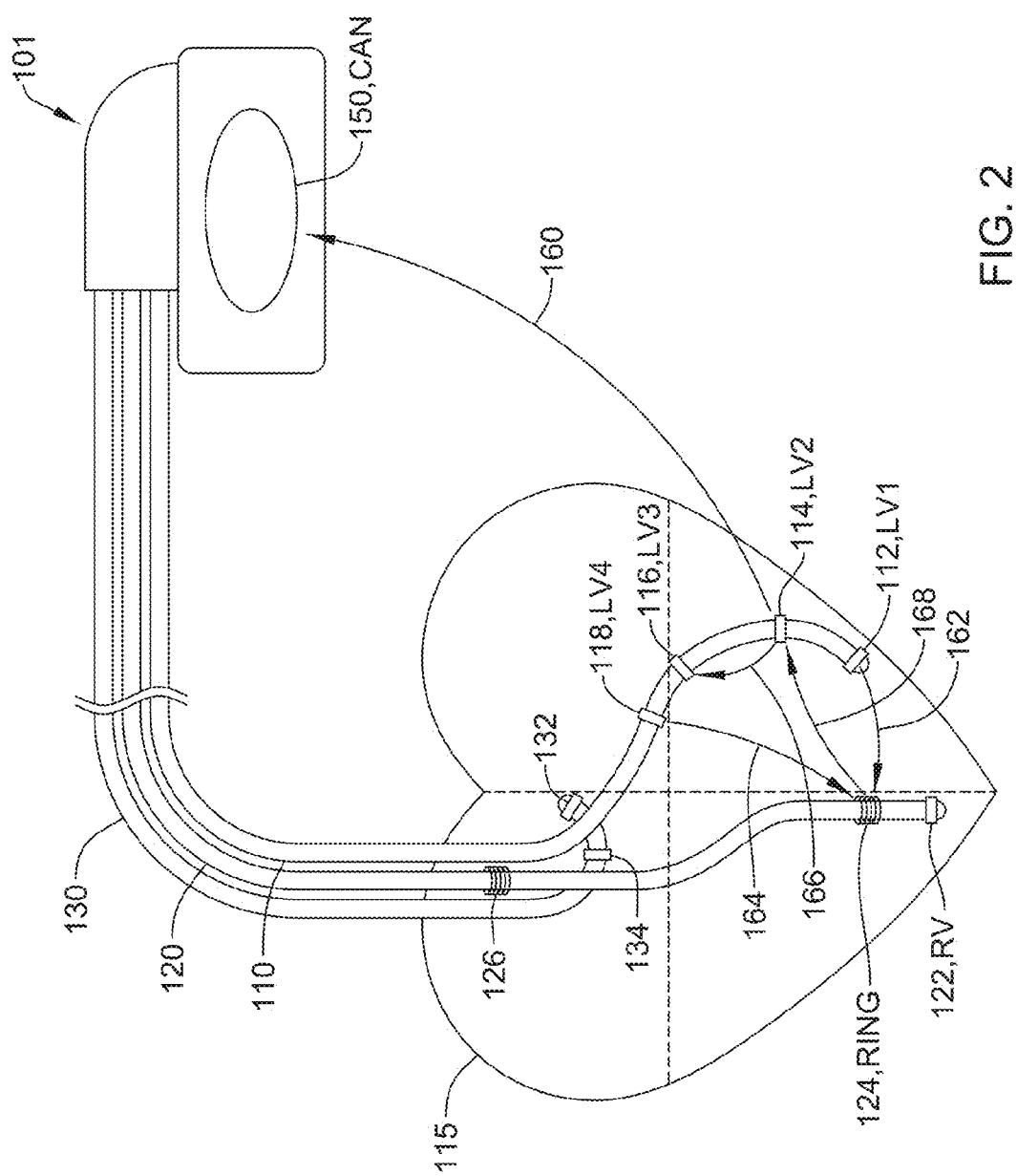
FIG. 2 is a schematic diagram of the implantable medical system of FIG. 1 showing various illustrative vectors.

FIG. 2 is a schematic diagram of the implantable medical system of FIG. 1 showing some exemplary vectors. As described with respect to FIG. 1, each pair of electro-stimulation electrodes of implantable medical device 101 may be considered a "vector". For each pair of electro-stimulation electrodes, a first one of the electro-stimulation electrodes is a cathode electrode and a second one of the electrodes is an anode electrode. In each of the illustrated example vectors, the arrow of each vector points to the anode electrode and the base of each arrow points to the cathode electrode. Although each vector is drawn as an arrow indicating a pathway, the vector only represents a general flow of electrical stimulation propagation when electrical stimulation is delivered via the particular vector. The exact pathway of electrical stimulation propagation will depend on many factors including physiological and physical system factors.

In some examples, implantable medical device 101 further includes a "can" electrode 150, as shown in FIG. 2. FIG. 2 further illustrates example vectors 160, 162, 164, 166, and 168. In FIG. 2, electro-stimulation electrodes 112, 114, 116, 118, 122, 124, and 150 are also labeled as LV1, LV2, LV3, LV4, RV, RING, and CAN (sometimes referred to in the art as Q), respectively, which are terms sometimes used in the art. Vector 160 represents the pair of the CAN electrode and the LV2 electrode, where the CAN electrode is an anode electrode and the LV2 electrode is a cathode electrode. The other vectors 162, 164, 166, and 168 all represent examples of vectors of implantable medical device 101. It should be understood that any combination of electro-stimulation electrodes may represent a unique vector. Additionally, each pair of electro-stimulation electrodes can actually produce two vectors because either of the pair of electro-stimulation electrodes can be the cathode electrode or the anode electrode. Table 1, below, lists all of the possible vectors of implantable medical device 101 comprising the RV, LV1, LV2, LV3, LV4, and CAN electrodes. The totality of possible vectors of implantable medical device 101 would further comprise combinations including electrodes 126, 132, 134, and RING. However, it should be understood that in other implantable medical device systems, particularly those with differing amounts of electrodes, the number of vectors of the system may be different. The example techniques described herein may be applicable to any such system including multiple electrodes.

TABLE 1

| Vector | Electrode Combination (Cathode Electrode → Anode Electrode) |
| --- | --- |
| Vector 1 (164) | LV1 → RV |
| Vector 2 | LV1 → LV4 |
| Vector 3 | LV1 → LV3 |
| Vector 4 | LV1 → LV2 |
| Vector 5 | LV1 → CAN |
| Vector 6 (184) | LV2 → RV |
| Vector 7 | LV2 → LV4 |
| Vector 8 | LV2 → LV3 |
| Vector 9 | LV2 → LV1 |
| Vector 10 (160) | LV2 → CAN |
| Vector 11 (182) | LV3 → RV |
| Vector 12 | LV3 → LV4 |
| Vector 13 (166) | LV3 → LV2 |
| Vector 14 | LV3 → LV1 |
| Vector 15 | LV3 → CAN |
| Vector 16 (162) | LV4 → RV |
| Vector 17 | LV4 → LV1 |
| Vector 18 | LV4 → LV2 |
| Vector 19 | LV4 → LV3 |
| Vector 20 | LV4 → CAN |
| Vector 21 | RV → LV1 |
| Vector 22 | RV → LV2 |
| Vector 23 (168) | RV → LV3 |
| Vector 24 | RV → LV4 |
| Vector 25 | RV → CAN |
| Vector 26 | CAN → RV |
| Vector 27 | CAN → LV1 |
| Vector 28 | CAN → LV2 |
| Vector 29 | CAN → LV3 |
| Vector 30 | CAN → LV4 |

Figure 3:
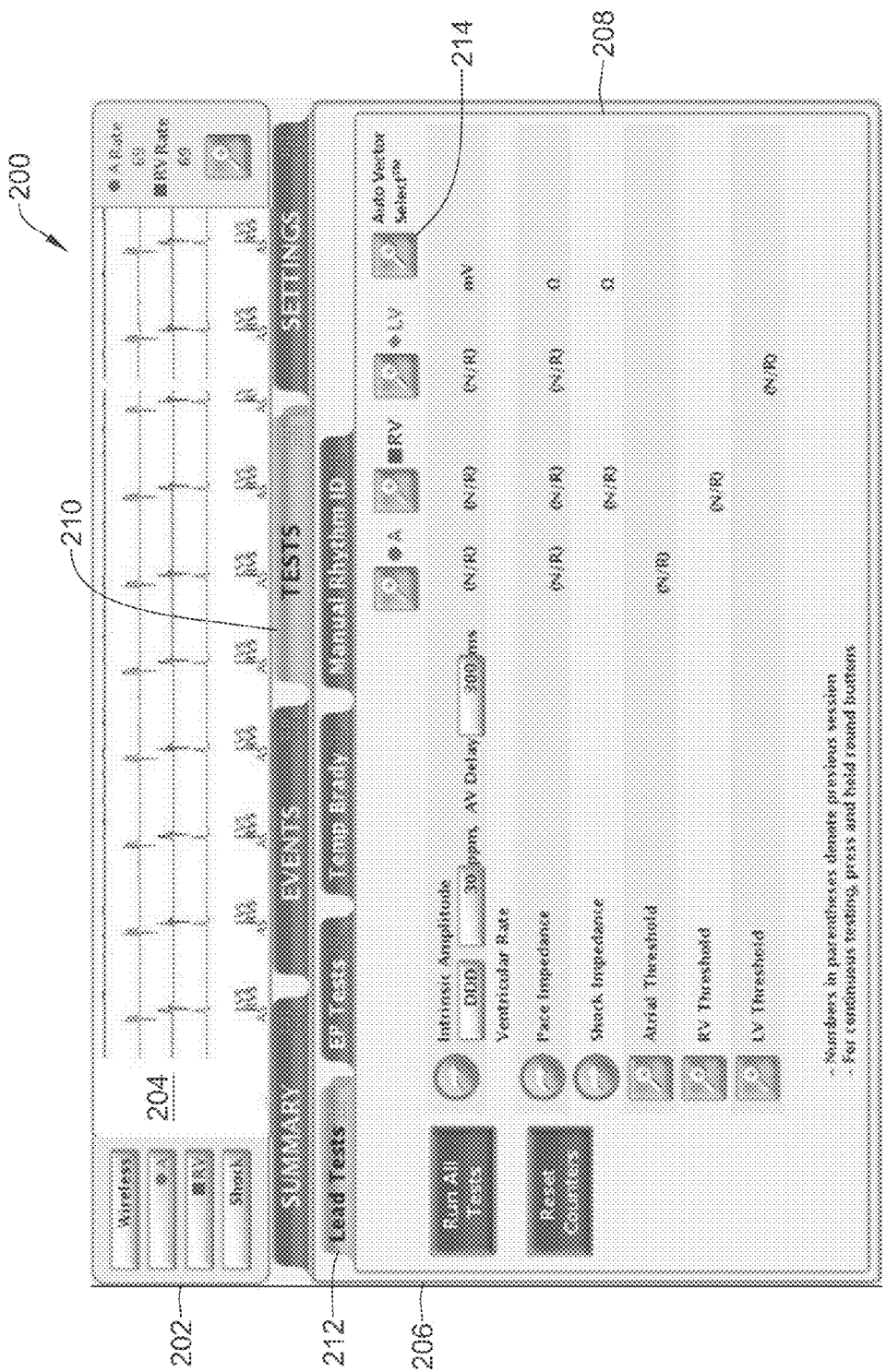
FIG. 3 is a graphical illustration of an illustrative graphical user interface (GUI) that may be displayed by the implantable medical system of FIG. 1.

FIG. 3 illustrates a graphical user interface (GUI) 200, which is an example graphical user interface that may be displayed to a user and used in conjunction with implantable medical device 101 and/or external assembly 140. For example, implantable medical device 101 or external assembly 140 may cause GUI 200 to be displayed at user interface 145 of external assembly 140. A user may interact with GUI 200 via an input device that is part of user interface 145, such as for example a keyboard, a mouse, a light pen, a touch-screen, a display screen, a printer, or an audio speaker.

In the example shown, GUI 200 may include a number of options for analyzing cardiac electrical data received from electrode system 107 and/or for programming implantable medical device 101. In the example shown, GUI 200 displays a data window 202, which includes data region 204. Data region 204 may include live or recorded cardiac electrical information of heart 115 detected by either implantable medical device 101 or external assembly 140. GUI 200 may also include window 206, with a first set of selectable tabs including "Tests" tab 210. In the example shown, upon selecting tests tab 210, GUI 200 may display sub-window 206 with a second set of selectable tabs. GUI 200 may indicate which particular selectable tabs are currently selected by displaying the selected tab or tabs in a dark/light and/or color contrast with respect to non-selected tabs. FIG. 3 displays an example of GUI 200 where, using an input device that is a part of user interface 145, a user has selected tests tab 210 and lead tests tab 212. FIG. 3 depicts GUI 200 after user has selected lead tests tab 212, where GUI 200 displays sub-window 206. Sub-window 206 may include a number of selectable buttons, including an auto vector select button 214.

Figure 4:
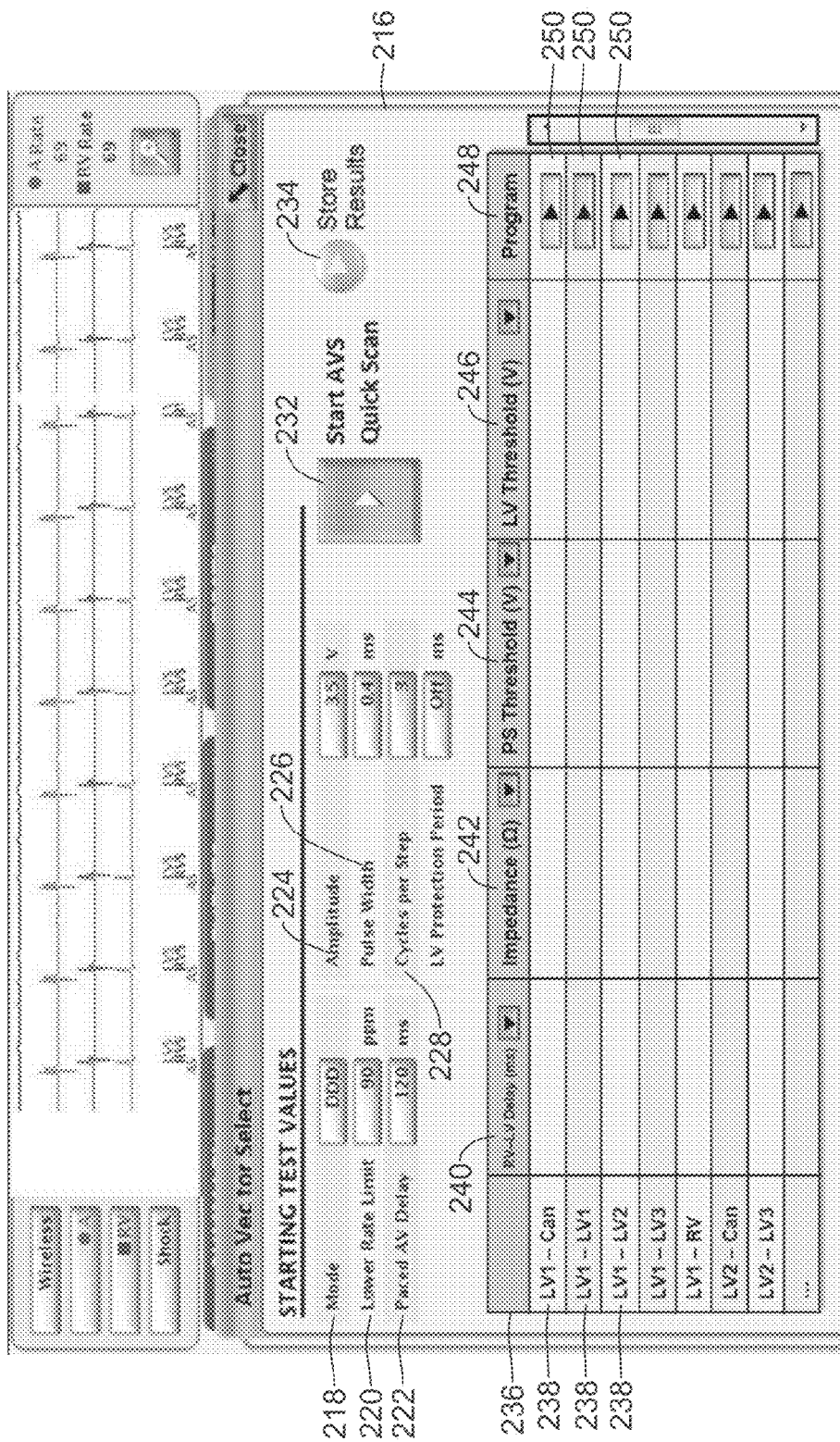
FIG. 4 is a graphical illustration of a GUI including an illustrative table of vectors that may be displayed by the implantable medical system of FIG. 1.

FIG. 4 illustrates an example display that GUI 200 may display upon receiving a selection of the auto vector select button 214. Upon receiving a selection of auto vector select button 214 (see FIG. 3), GUI 200 may open up a new window, such as auto vector select window 216. Auto vector select window 216 may include a number of features. For example, auto vector select window 216 may include test parameters for administering a vector assessment or scan. Some example test parameters may include, for instance, mode 218, lower rate limit 220, paced AV delay 222, amplitude 224, pulse width 226, cycles per step 228, and LV protection period 230. Each of these parameters may be configurable by the user, if desired. In some cases, selecting one of the parameters may allow a user to select a value from a drop down menu or input a value directly into a field.

Mode 218 represents a type of pacing that will be applied during one or more vector scans. Lower rate limit 220 represents a minimum number of pacing pulses per minute that will be delivered during the scan. In the example of FIG. 2, lower rate limit 220 is set to 90, meaning that throughout the scan, while the pacing pulses per minute may vary throughout the scan, the delivered rate of pacing pulses will not fall below 90 pulses per minute. Amplitude 224 represents, in voltage terms, the amplitude of the pacing pulses that will be delivered during a scan. Pulse width 226 represents the pulse width of delivered pulses. For example in FIG. 4, pulse width 226 is set to 0.4 ms, indicating that each individual delivered pulse will be 0.4 ms long. Cycles per step 228 indicates how many pacing pulses will be delivered via each vector per step. For example, one scan "cycle" may include delivering three pacing pulses per vector to each vector. In FIG. 4, cycles per step 228 is set to three, which indicates that for each step, implantable medical device 101 or external assembly 140 will perform three cycles. In other examples, the amount of delivered pacing pulses per cycle may be one, two, four, or any number of pacing pulses. LV protection period 230 sets a period of time for the device or system performing the vector scan to pause the scan and deliver electrical stimulation to the left ventricle of heart 115 sufficient to cause the left ventricle to contract, thereby ensuring blood flow during the scan.

GUI 200 may additionally include a table 236. Illustrative Table 236 is configured to display a list of vectors 238 in separate rows and a list of parameters in separate columns. The list of vectors 238 may include all, or only a portion, of potential vectors of system 100. In some examples, the list of vectors 238 may include all of the vectors listed in Table 1 above. One parameter that GUI 200 may display in table 236 is RV-LV delay, such as in RV-LV delay column 240.

The values of cells of RV-LV delay column 240 may represent determined electrical delays between a cathode electro-stimulation electrode of a vector and an anode electro-stimulation electrode of the vector. In some examples, GUI 200 may display values in the cells of RV-LV delay column 240 with units of milliseconds. Other examples may display values in the cells of RV-LV delay column 240 in other time units, as desired.

Another parameter that GUI 200 may display in table 236 is impedance, such as in impedance column 242. GUI 200 may display values in cells of impedance column 242 with units of ohms. The values of impedance in the cells of impedance column 242 may represent the value of a determined impedance between the two electro-stimulation electrodes of a vector.

Figure 5:
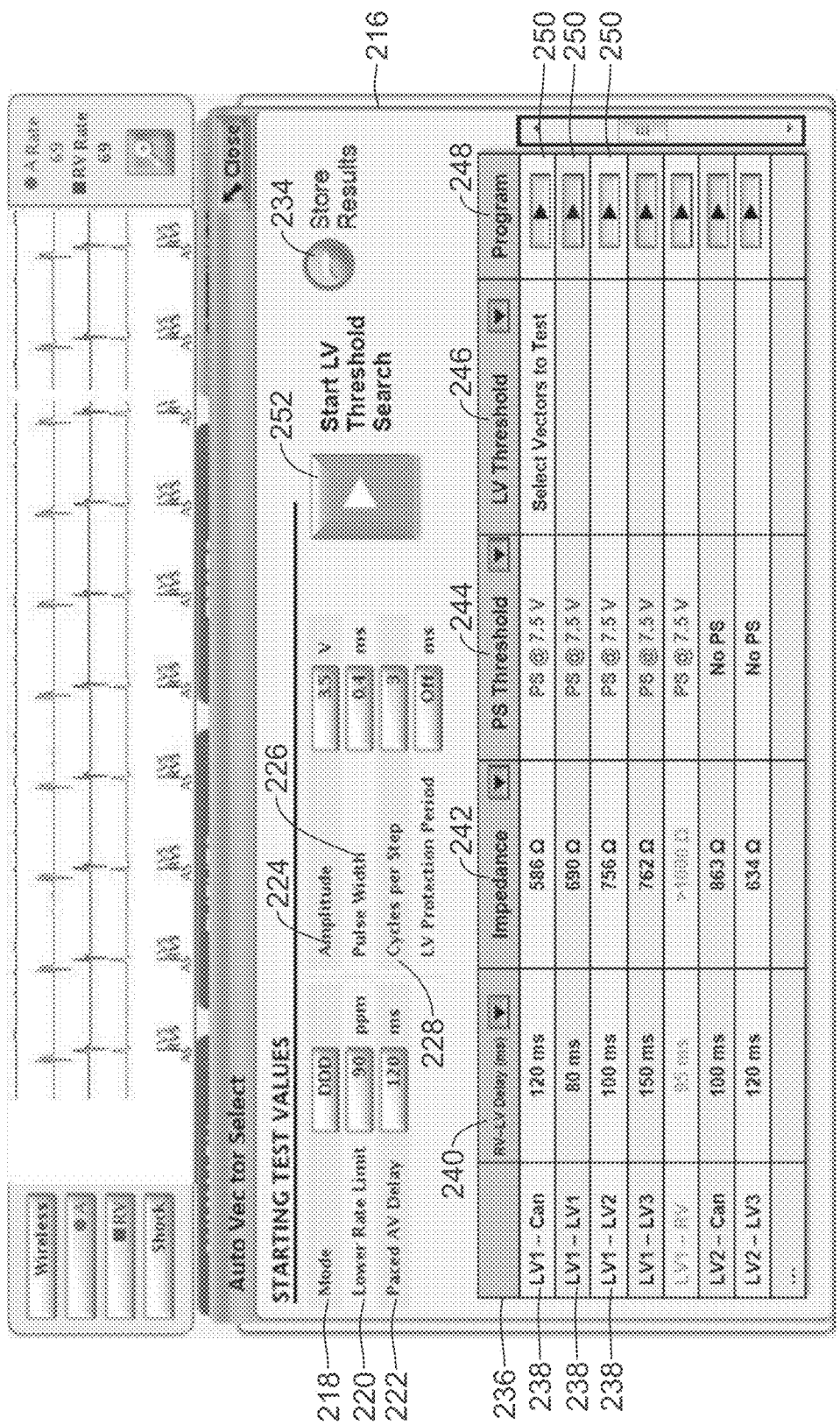
FIG. 5 is a graphical illustration of a GUI including an illustrative table of vectors that may be displayed by the implantable medical system of FIG. 1.

PS threshold column 244 contains cells whose values may indicate a determined presence of phrenic nerve stimulation. In some examples, if phrenic nerve stimulation is detected while delivering electrical stimulation via a particular vector, GUI 200 may display a 'YES' value in the appropriate cell of PS threshold column 244. Similarly, if phrenic nerve stimulation is not detected while delivering electrical stimulation via a particular vector, GUI 200 may display a 'NO' value in the appropriate cell of PS threshold column 244. In other examples, if phrenic nerve stimulation is detected while delivering electrical stimulation via a particular vector, GUI 200 may display a 'PS' value along with the lowest delivered voltage at which implantable medical device 101 or external assembly 140 detected a presence of phrenic nerve stimulation. This value may be termed a phrenic nerve stimulation threshold value. An example of this type of display may be seen in FIG. 5, where GUI 200 displays 'PS @ 7.5 V' value in cells corresponding to vectors where implantable medical device 101 or external assembly 140 detected a presence of PS while delivering electrical stimulation via those vectors at 7.5 V. In other examples, GUI 200 may display other values or representations that indicate other information, i.e. information that informs a user of a presence of phrenic nerve stimulation and/or a presence of phrenic nerve stimulation at a particular voltage of delivered electrical stimulation.

In other examples, table 236 may include other or additional columns representing different or additional parameters. For instance, in some examples, table 236 may include an energy parameter column. For example, values of cells of such an energy parameter column may represent an amount of energy required for a delivered stimulation pulse to capture heart 115 for each of vectors 238. In other examples, values in an energy column may represent the estimated time period for how long a battery of system 100 will last if implantable medical device 101 delivers electrical stimulation therapy via the corresponding vectors.

In still other examples, table 236 may include, for example, a sense amplitude column. Values in a sense amplitude column may represent an amplitude (in voltage) of a sensed signal from heart 115 for each of vectors 238. For example, the amplitude of the sensed signal may be the difference in voltage between a peak and a trough of a QRS complex. In some examples, the amplitude of a sensed signal may be indicative of the quality of a contact between the electro-stimulation electrodes and the myocardium of heart 115.

In some instances, and with reference to FIG. 4, GUI 200 may display a start AVS quickscan button 232 in auto vector select window 216. Upon selection of start AVS quickscan button 232, implantable medical device 101 or external assembly 140, or a combination of implantable medical device 101 and external assembly 140, may initiate a scan of vectors 238 listed in table 236. In one example, a first selection of start AVS quickscan button 232 may cause implantable medical device 101 or external assembly 140 to measure the RV-LV delay for each of vectors 238. In order to measure RV-LV delay, implantable medical device 101 or external assembly 140 may deliver electrical stimulation to a first electro-stimulation electrode of each vector and determine an elapsed time before detecting the delivered electrical stimulation at the second electro-stimulation electrode of each vector. GUI 200 may subsequently display each of the determined RV-LV delays in table 236. In other examples, implantable medical device 101 or external assembly 140 may deliver electrical stimulation to a first electro-stimulation electrode and measure the elapsed time before detecting electrical activation of heart 115 or a contraction of heart 115.

Upon a second selection of start AVS quickscan button 232, implantable medical device 101 or external assembly 140 may initiate a scan of vectors 238 to determine an impedance of each vector. In order to determine the impedance for each vector, implantable medical device 101 or external assembly 140 may deliver a voltage pulse to a first electro-stimulation electrode of a vector and measure a current flow between the first and second electro-stimulation electrodes of the vector. Using Ohm's Law, $Z=V/I$, implantable medical device 101 or external assembly 140 may determine an impedance for each vector. Alternatively, implantable medical device 101 or external assembly 140 may deliver a current pulse to a first electro-stimulation electrode of a vector and measure the resulting voltage differential between the first and second electro-stimulation electrodes of the vector and use Ohm's Law to determine impedance. Again, GUI 200 may display the determined impedance value of each vector in table 236.

Upon a third selection of start AVS quickscan button 232, implantable medical device 101 or external assembly 140 may initiate a scan of vectors 238 to determine a presence of phrenic nerve stimulation. For example, implantable medical device 101 or external assembly 140 may deliver electrical stimulation via each vector and detect whether the delivered electrical stimulation stimulated the phrenic nerve. In some examples, implantable medical device 101 or external assembly 140 may deliver electrical stimulation via each vector at a number of different voltage amplitudes. In still other examples, implantable medical device 101 or external assembly 140 may deliver electrical stimulation to detect a presence of phrenic nerve stimulation only at a maximum or other predefined voltage amplitude. Implantable medical device 101 or external assembly 140 may determine at which voltage amplitudes implantable medical device 101 or external assembly 140 detected a presence of phrenic nerve stimulation for each vector. GUI 200 may display determinations of phrenic nerve stimulation in table 236, in accordance with the techniques disclosed above. In some instances, GUI 200 may display either a 'YES' value if implantable medical device 101 or external assembly 140 detected phrenic nerve stimulation at any voltage amplitude. Alternatively, in other examples, GUI 200 may display a value or representation that conveys at which voltages implantable medical device 101 or external assembly 140 detected presence of phrenic nerve stimulation. In some examples, GUI 200 may display a value or representation of just the lowest voltage amplitude where implantable medical device 101 or external assembly 140 determined a presence of phrenic nerve stimulation. In some examples, this value may be termed a phrenic nerve stimulation threshold value.

In some instances, upon receiving a single selection of start AVS quickscan button 232, implantable medical device 101 or external assembly 140 may perform a single scan of vectors 238 and determine all three parameters. In still other examples, upon receiving a single selection of start AVS quickscan button 232, implantable medical device 101 or external assembly 140 may perform successive scans of vectors 238, without receiving additional input, to determine all three of parameters RV-LV delay, impedance, and presence of phrenic nerve stimulation. In still other examples, upon receiving a single selection of start AVS quickscan button 232, implantable medical device 101 or external assembly 140 may perform a scan of vectors 238 to determine two of the three parameters, with an additional selection of start AVS quickscan button 232 needed before performing a second scan to determine the third of the three parameters. In some examples, implantable medical device 101 or external assembly 140 may perform one or more scans in accordance with the techniques disclosed in commonly assigned and co-pending provisional application titled "SYSTEMS AND METHODS FOR DETERMINING PARAMETERS FOR EACH OF A PLURALITY OF VECTORS" filed on Dec. 18, 2013, the entirety of which has been incorporated herein by reference.

In other examples, after receiving a selection of start AVS quickscan button 232, implantable medical device 101 or external assembly 140, or a combination of implantable medical device 101 and external assembly 140, may cause GUI 200 to display a table, drop down menu, or other element in GUI 200 that lists one or more predefined groups of vectors. In other examples, GUI 200 may display one or more predefined group buttons proximate table 236. Upon receiving a selection, either of one or more of the predefined groups in a table, drop down menu, or other element in GUI 200, or a selection of one or more predefined group buttons, implantable medical device 101 or external assembly 140 may select all vectors comprising the predefined group or groups. For example, one predefined group may consist only of vectors that include LV1 electrode. Another predefined group may consist of only vectors that include LV2 electrode. Accordingly, such predefined groups may consist of predefined subsets of vectors 238. Such selection options may allow a user to quickly select only particular vectors of interest to be tested, which may save time by only performing tests on vectors that are already known to be of interest.

In the example shown, GUI 200 also displays a store results button 234. Upon receiving a selection of store results button 234, implantable medical device 101 or external assembly 140 may store the results of previous scans into a memory, such as memory circuit 104 of implantable medical device 101 or memory 144 of external assembly 140. GUI 200 may further display another parameter, LV threshold 246, in another column, program column 248, and program buttons 250, which will be described in further detail below.

Figure 6:
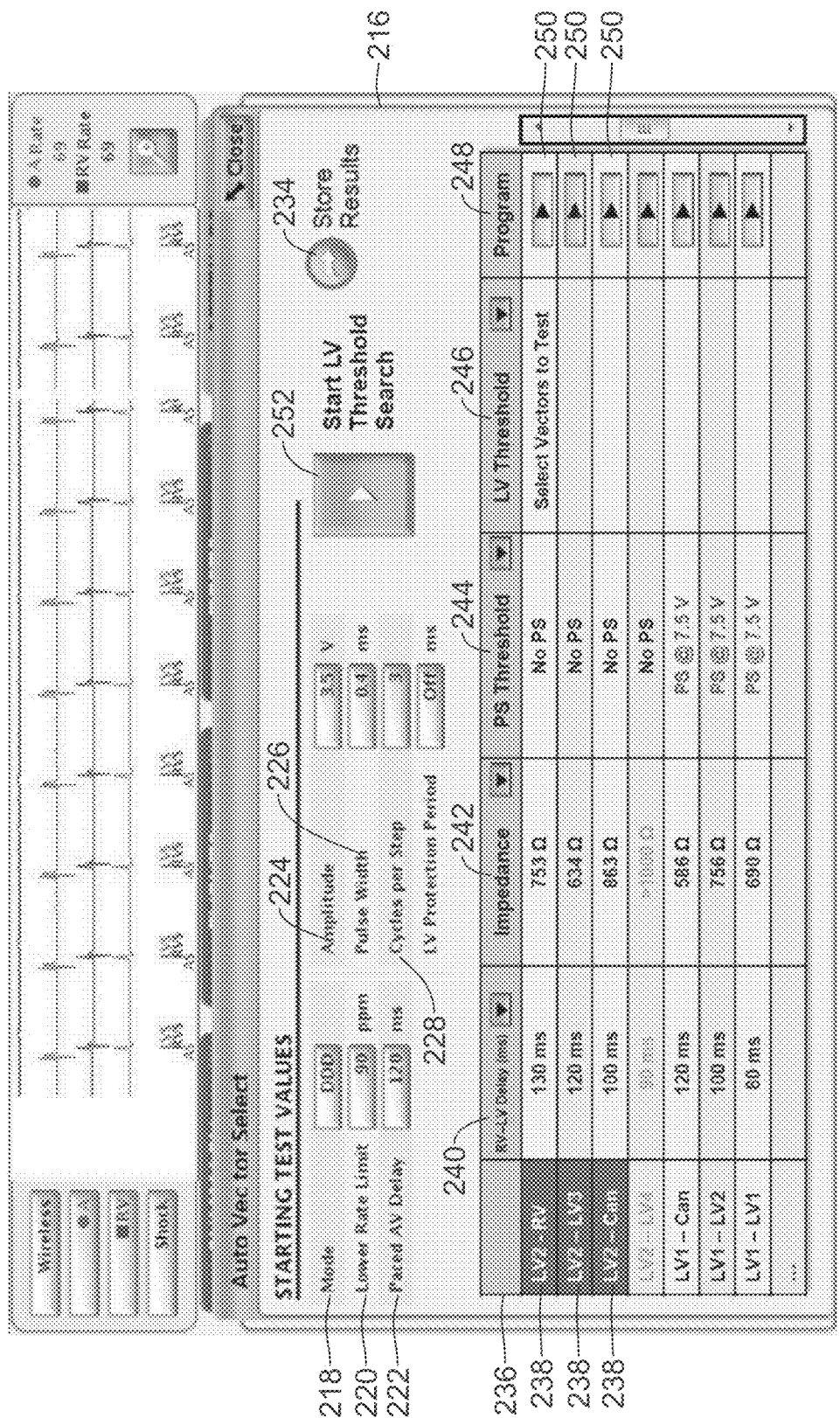
FIG. 6 is a graphical illustration of a GUI including an illustrative selectable table of vectors that may be displayed by the implantable medical system of FIG. 1.

FIG. 6 illustrates an example of GUI 200 after implantable medical device 101 or external assembly 140 has performed one or more vector scans. GUI 200, in FIG. 6, displays the results after implantable medical device 101 or external assembly 140 has determined values for RV-LV delay, impedance, and presence of phrenic nerve stimulation for each of vectors 238. In the example shown in FIG. 6, each of the values in the cells of RV-LV delay column 240 and impedance column 242 are displayed with a numerical value. For example, for vector LV1-CAN, GUI 200 displays values of 120 ms in the corresponding cell of RV-LV delay column 240 and 586 ohms in the corresponding cell of impedance column 242. However, in other examples, GUI 200 may display non-numerical values for impedance, or a mix of numerical and non-numerical values. For example, in some instances, it is not necessary to display a numerical value for impedance. Rather, GUI 200 may display a first value if the impedance of a vector is equal to or above an impedance threshold and a second value if the impedance of a vector is below an impedance threshold. For example, GUI 200 may display the value 'OK' in impedance column 242 if the impedance value determined by implantable medical device 101 or external assembly 140 is below an impedance threshold and a 'HIGH' value if the impedance of a vector is equal to or above an impedance threshold. Of course, in other examples, other values or symbols (like a check mark) may be used to convey similar information. In still other examples, GUI 200 may display vectors with impedance values higher than an impedance threshold in a highlighted or other dark/light or color contrasted manner.

Figure 9:
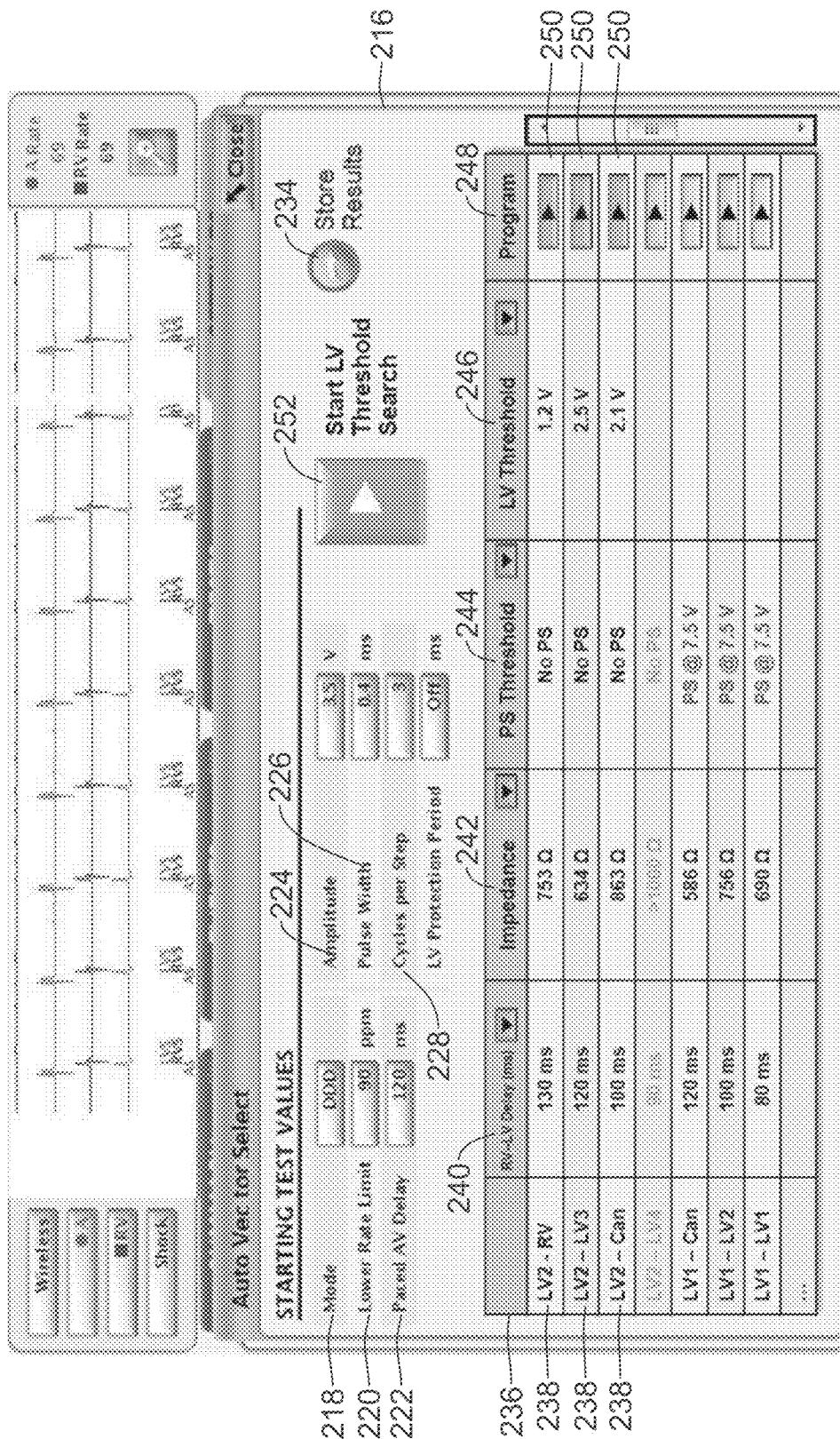
FIG. 9 is a graphical illustration of a GUI including an illustrative sortable table of vectors which may be displayed by the implantable medical system of FIG. 1.

In the example shown, after a RV-LV delay, impedance, and presence of phrenic nerve stimulation have been determined for each of vectors 238, and values populated into RV-LV delay column 240, impedance column 242, and PS threshold column 244, GUI 200 may change start AVS quickscan button 232 into start LV threshold search button 252. Upon receiving a selection of start LV threshold search button 252, implantable medical device 101 or external assembly 140 may determine an LV threshold for each of vectors 238. In determining an LV threshold, implantable medical device 101 or external assembly 140 may deliver electrical stimulation via a vector at a first voltage amplitude and detect whether the delivered electrical stimulation captured heart 115, causing a contraction of heart 115. Implantable medical device 101 or external assembly 140 may proceed to deliver electrical stimulation via the same vector at one or more additional voltage amplitudes. For example, the first voltage amplitude may be relatively high (e.g., 7V, 8V, 9V, 10V, or any other voltage), and implantable medical device 101 or external assembly 140 may deliver electrical stimulation at decreasing voltage amplitudes in various increments (e.g., 0.2V, 0.25V, 0.5V, 1V, or any other increment) down to amplitude 224. In other examples, the first voltage amplitude may be amplitude 224, and implantable medical device 101 or external assembly 140 may deliver electrical stimulation at increasing voltage amplitudes up to a voltage where implantable medical device 101 or external assembly 140 detects capture of heart 115, or up to a maximum voltage amplitude. Implantable medical device 101 or external assembly 140 may record the lowest voltage amplitude at which the delivered electrical stimulation captured the heart 115. GUI 200 may then display any determined results, for example the lowest voltage amplitude at which the delivered electrical stimulation captured heart 115, in the LV threshold column 246 (as seen in FIG. 9). Implantable medical device 101 or external assembly 140 may perform a similar process or processes for each vector.

In some instances, GUI 200 may display table 236 with binary values for any of parameters RV-LV delay, impedance, and/or presence of phrenic nerve stimulation. For example, each parameter may have an associated parameter threshold, wherein GUI display a first value in table 236 when a parameter is less than the threshold and a second value if the parameter is greater than or equal to the threshold. Each parameter may have different associated parameter thresholds and, in some examples, different binary values or representations indicating the value of the parameter relative to the parameter's associated threshold.

In still other examples, GUI 200 may not display absolute values in cells of table 236 for some or any of parameters RV-LV delay, impedance, and/or presence of phrenic nerve stimulation. In some instances, GUI 200 may display a value of a given parameter as relative to a different parameter. For example, GUI 200 may display whether a particular value of a parameter is higher or lower than a threshold, as described above. In other examples, GUI 200 may display whether a value of a parameter is higher or lower than an average of values for that parameter across all of vectors 238 for which implantable medical device 101 or external assembly 140 determined that parameter. In still other examples, GUI 200 may display values of a parameter as relative to some other value.

A user may additionally select one of the vectors and select a corresponding program button 250 in program column 248. Selecting one of program buttons 250 may cause implantable medical device 101 or external assembly 140 to program implantable medical device 101 to deliver electrical stimulation via the selected vector. Another example may include an additional step in which a new dialog box opens to allow the user to select a corresponding voltage amplitude and pulse width that will be programmed into medical device 101. Implantable medical device 101 may then be configured to deliver electrical stimulation via the selected vector at the selected voltage amplitude and pulse width. This dialog box may contain the previously measured LV capture threshold for reference, and fields to allow the user to select the desired voltage and pulse width to be programmed.

FIG. 6 illustrates an example of three selected vectors. FIG. 6 illustrates GUI 200 with vectors LV2-RV, LV2-LV3, and LV2-CAN of vectors 238 selected by a user. In the example shown, GUI 200 may display the selected vectors with dark/light or color contrast with respect to non-selected vectors. In some cases, GUI 200 may display the dark/light or color contrast for the entire row corresponding to a selected vector or just one or few cells in that row. In the example of FIG. 6, GUI 200 displays selection of vectors LV2-RV, LV2-LV3, and LV2-CAN after either implantable medical device 101 or external assembly 140 has already determined RV-LV delay, impedance, and presence of phrenic nerve stimulation for each of vectors 238. Accordingly, in such an example, a selection of start LV threshold search button 252 may result in a determination of an LV threshold for only the selected vectors. In some examples, a user may select vectors at prior times to determining one or more of RV-LV delay, impedance, and presence of phrenic nerve stimulation parameters. For instance, in examples where implantable medical device 101 or external assembly 140 determines each of RV-LV delay, impedance, and presence of phrenic nerve stimulation parameters separately, such as when only a single parameter is determined for each selection of start AVS quickscan button 232, a user may select a number of vectors after each scan for a subsequent scan. Implantable medical device 101 or external assembly 140 may then only perform the subsequent scan or scans for those selected vectors. In this manner, based on results of a first scan, a user may eliminate vectors from subsequent tests, e.g., by selecting fewer than all vectors, in order to decrease the time taken for subsequent scans.

Figure 7:
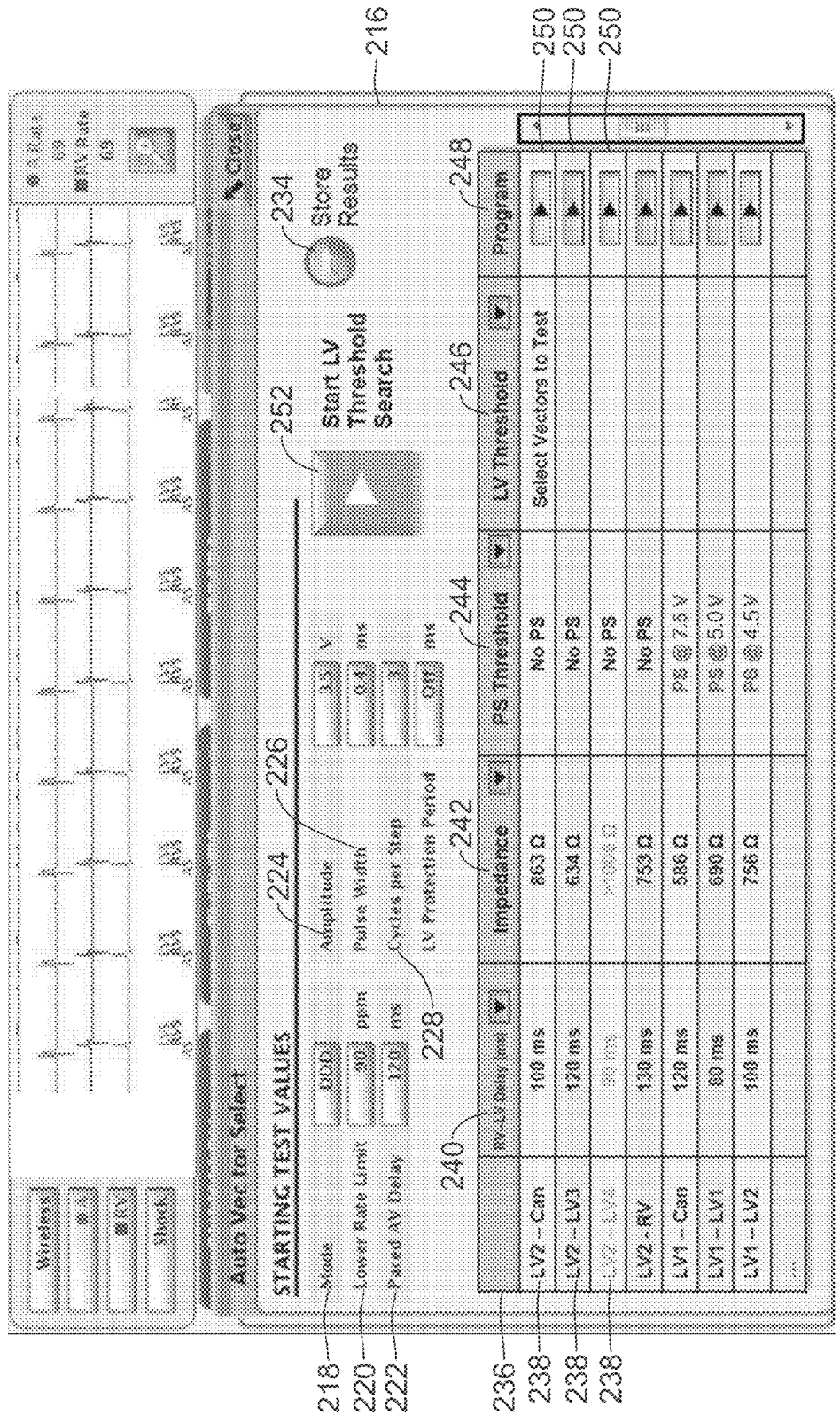
FIG. 7 is a graphical illustration of a GUI including an illustrative sortable table of vectors that may be displayed by the implantable medical system of FIG. 1.

In order to facilitate easier viewing and selection of vectors, table 236 may support one or more sorting functions. For example, a user may be able to sort each of RV-LV delay column 240, impedance column 242, PS threshold column 244, and/or LV threshold column 246. In some examples, a user may select the top cell of each column in order to sort by that column. For example, a user may select the top cell of PS threshold column 244 labeled "PS Threshold" in order to sort vectors 238 by the value of their corresponding cells in the PS threshold column 244. FIG. 6 shows the vectors sorted by the PS threshold column 244, showing those vectors that did not have phrenic stimulation at 7.5 V. Likewise, FIG. 7 illustrates GUI 200 after a user has sorted table 236 by PS threshold column 244. In examples where PS threshold column 244 contains cells that have binary values (whether numeric or non-numeric), sorting vectors 238 by PS threshold column 244 may result in two groupings of vectors 238, with all of vectors 238 with a first value listed above all of vectors 238 with a second value in table 236. Selecting the top cell of PS threshold column 244 labeled "PS Threshold" a second time may reverse the order of the groupings of vectors 238 such that all of vectors 238 with the second value are listed above all of vectors 238 with the first value.

In examples where the values in the cells of PS threshold column 244 are not binary, sorting table 236 by PS threshold column 244 may result in a plurality of groups of vectors wherein each grouping is displayed relative to each other grouping in an ascending or descending sorted manner. For example, in the example of FIG. 7, if additional vectors of vectors 238 have values in their corresponding cells in PS threshold column 244 such as 'PS @ 5.0 V' or 'PS @ 4.0 V', table 236 may have four separate groups of vectors. For example, vectors 238 with 'NO PS' values may be listed above all other vectors. Vectors 238 with 'PS @ 7.5 V' may be listed below the vectors with values of 'NO PS' but above all remaining vectors. Vectors 238 with values of 'PS @ 5.0 V' may be listed below vectors 238 with values of 'PS @ 7.5 V', as 5 is less than 7. Likewise, vectors 238 with values of 'PS @ 4.5 V' may be listed at the bottom of table 236. Again, selecting the top cell of PS threshold column 244 may reverse the sorting, with vectors 238 with values of 'PS @ 4.5 V' listed at the top of table 236.

Figure 8:
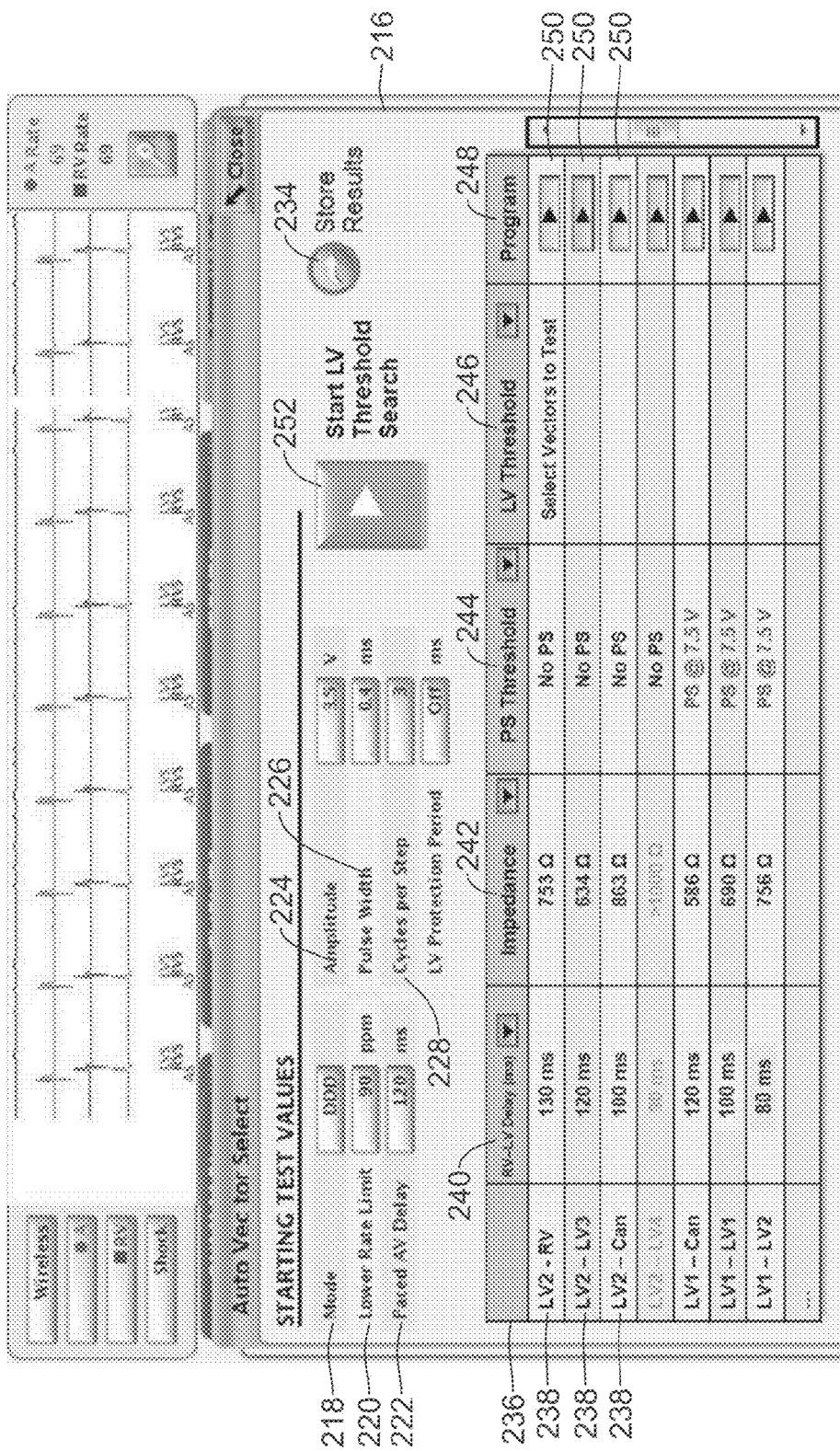
FIG. 8 is a graphical illustration of a GUI including an illustrative sortable table of vectors that may be generated by the implantable medical system of FIG. 1.

In some examples, after selecting the top cell of a first column to sort by, a user may subsequently select a second column to sort by. FIG. 8 depicts GUI 200 after a user has selected the top cell of RV-LV delay column 240 to sort by RV-LV delay column 240 subsequent to sorting by PS threshold column 244. In the example of FIG. 8, selecting a second column to sort by after selecting and sorting by a first column retains the sorting of the first column. For example, after selecting the top cell of RV-LV delay column 240 to sort by RV-LV delay column 240, vectors 238 are still displayed in groups according to the first sorting by PS threshold column 244, e.g. vectors 238 are still sorted into a first group with values of 'NO PS' in PS threshold column 244 and a second group with values of 'PS @ 7.5 V.' After receiving a selection from a user to sort by a second column, GUI 200 may display table 236 with each group of vectors 238, determined by a first sorting, sorted by the values in cells of the second column. In the example of FIG. 8, GUI 200 displays the first group of vectors 238 in table 236, i.e. vectors with values of 'NO PS' in PS threshold column 244, sorted in a descending order of each vector's value in RV-LV delay column 240 separately from the second group of vectors 238, i.e. vectors with values of 'PS @ 7.5 V' in PS threshold column 244. In FIG. 8, GUI 200 additionally displays each of vectors 238 with values of 'PS @ 7.5 V' in PS threshold column 244 as sorted in a descending order separately from the first group of vectors 238. Accordingly, in some examples, selecting a second column to sort by after selecting a first column to sort by results in a sorting of vectors 238 by the first column. Then, each vector 238 within each grouping of vectors with the same value in the first column are additionally sorted by each vector's value in the second column.

In other examples, vectors 238 may be sorted a third time by values in a third column in a manner similar to sorting by a second column. For example, if a user selects a third column of table 236 by which to sort and there are groups of vectors 238 with equivalent values in both the first and second columns, each of those groups, i.e. vectors 238 that have equivalent values in the first and second columns, may further be sorted according to their values in the third column, for example in an ascending or descending order based on the values in the third column.

In still other examples, a user may select one or more of vectors 238 in table 236. After selecting one or more vectors 238, a user may then select one or more columns by which to sort. In such examples, after receiving a selection of one or more vectors 238 and a selection of a column by which to sort, e.g. by receiving a selection of a top cell of a column of table 236, for example impedance column 242, GUI 200 may display table 236 with only the selected vectors sorted according to the selected column. In some examples, GUI 200 may display the selected vectors at the top of table 236 and sorted according to the selected column.

In other examples, GUI 200 may contain a button that will undo all previous sorting and list all vectors 238 by their original listing disregarding all values in the columns. Another example would be to allow the user to sort the entire table by the first column of vector names, which would disregard all other sorts and just arrange all rows by vector name.

The above examples described sorting according to PS threshold column 244 and then RV-LV delay threshold 240. Other examples may employ similar sorting techniques after receiving selections to sort by impedance column 242 and then by RV-LV delay column 240. Still other examples may employ similar sorting techniques after receiving selections to sort by LV threshold column 246 and then by PS threshold column 244. Generally, the systems and devices described herein may use the disclosed techniques with any column or combinations of columns. Sorting vectors according to the disclosed techniques may help users quickly identify desirable vectors for delivering electrical stimulation to heart 115.

The above description centered on GUI 200 and the various features of GUI 200 may display, such as test values, scan buttons, and table 236, including the specific presentation of vectors 238 within table 236 according to user selections. In some examples, implantable medical device 101 may receive the selections from a user, such as via communication circuit 102. For example a user may enter user input, for example selections of various buttons displayed by GUI 200 or cells of table 236, into user interface 145 of external assembly 140 and external assembly 140 may communicate the user input to communication circuit 102 of implantable medical device 101.

Communication circuit 102 may further communicate the user input to processor circuit 103. Processor 103 may then process the user input, for example by performing a sorting of vectors 238 of table 236 or causing GUI 200 to display various features with dark/light and/or color contrast. Processor circuit 103 may then cause user interface 145 to display an updated GUI 200 according to the user input, for example by communicating with user interface 145 via communication circuit 102 and communication circuit 142. In other examples, processor circuit 143 of external assembly 140 may process the user input and cause user interface 145 to display and update GUI 200 according to the user input. In still other examples, processor circuit 103 and processor 143 may work in cooperation to process the user input and cause user interface 145 to display and updated GUI 200 according to the user input.

FIG. 9 illustrates GUI 200 after implantable medical device 101 or external assembly 140 has received user input that selects the first three vectors in the table and the user has hit the Start LV Threshold Search button 252. In the example shown, FIG. 9 shows GUI 200 after implantable medical device 101 or external assembly 140 has received a selection of vectors LV2-RV, LV2-LV3, and LV2-CAN and a selection of start LV threshold search button 252. In response, implantable medical device 101 or external assembly 140 has run an LV threshold scan on the selected vectors, and GUI 200 displays the results of the scan in LV threshold column 246. The displayed results represent a lowest voltage at which delivered electrical stimulation captured the heart. In other examples, where a user has not selected any vectors, selecting start LV threshold search button 252 may result in implantable medical device 101 or external assembly 140 performing an LV threshold scan for each vector 238 of table 236. In still other examples, GUI 200 may display start LV threshold search button 252 in addition to start AVS quick-scan button 232. In such examples, selecting start LV threshold search button 252 may start an LV threshold scan and determine LV capture thresholds even though implantable medical device 101 or external assembly 140 has not performed one or more scans to determine RV-LV delay, impedance, and/or a presence of phrenic nerve stimulation.

Figure 10:
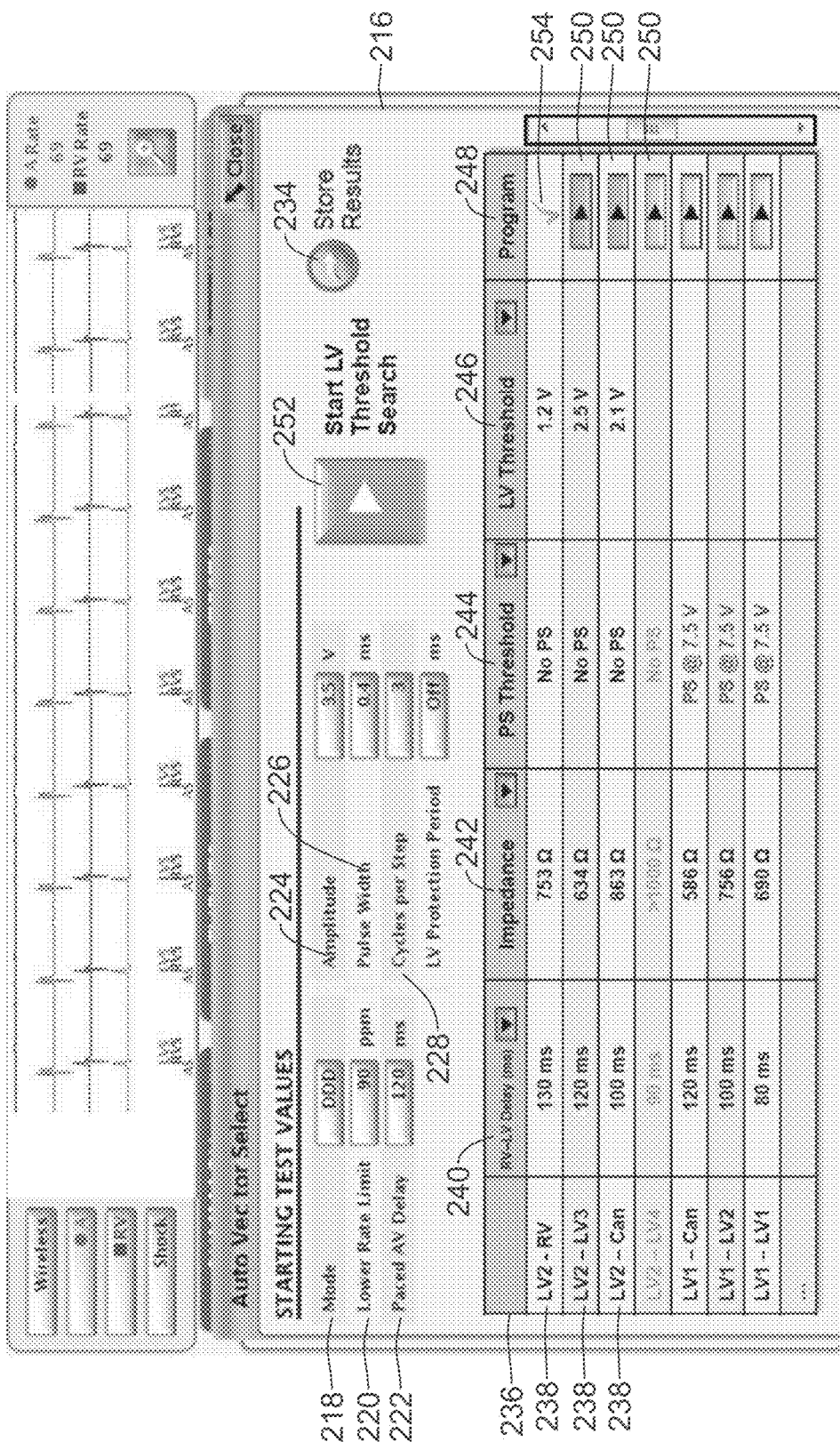
FIG. 10 is a graphical illustration of a GUI that allows a user to select a particular vector from a table of vectors for programming of a medical device system such as the implantable medical system of FIG. 1.

FIG. 10 displays an example of GUI 200 after implantable medical device 101 or external assembly 140 has received a selection of one of program buttons 250 in program column 248. After receiving a selection of one of program buttons 250, implantable medical device 101 or external assembly 140 may cause GUI 200 to change the selected one of program buttons 250 to a different graphical representation, such as check-mark 254 as shown. As described above, after receiving a selection of one of program buttons 250, implantable medical device 101 or external assembly 140 may program implantable medical device 101 to deliver electrical stimulation via the vector associated with the selected one of program buttons 250 (e.g., the vector in the same row as the first one of program buttons 250). In some examples, selecting a second one of program buttons 250 may override any previous programming of implantable medical device 101. For example, selecting a second one of program buttons 250 may cause GUI 200 to display the second selected one of program buttons 250 with a different graphical representation as the rest of program buttons 250, for example similarly to check-mark 254. Additionally, GUI 200 may change the graphical representation of the first selected one of program buttons 250 back to be similar to the rest of program buttons 250. In some examples, implantable medical device 101 or external assembly 140 may further program implantable medical device 101 to deliver electrical stimulation via the vector associated with the second selected one of program buttons 250 and not deliver electrical stimulation via the vector associated with the first selected one of program buttons 250.

Figure 11:
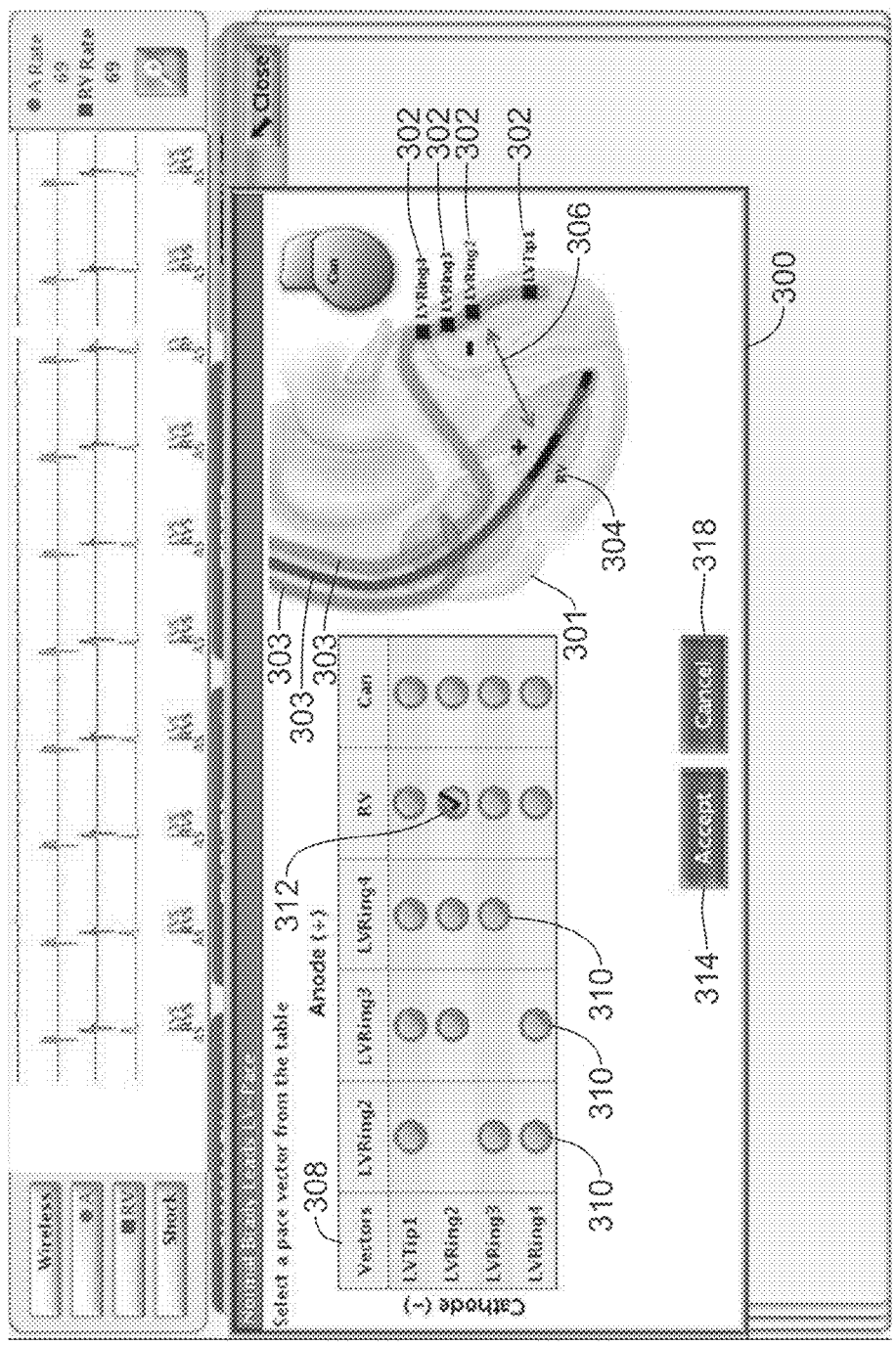
FIG. 11 is a graphical illustration of a GUI including a schematic illustration of a heart and the selected vector that may be generated by the implantable medical system of FIG. 1.

FIG. 11 is a representation of a graphical user interface window 300 that may be displayed by user interface 145. In some examples, user interface 145 may display user interface window 300 after receiving a selection of one of program buttons 250 in FIG. 10, but before changing the graphical representation of the selected program button 250. For example, user interface window 300 may include one or more parameters that need to be selected by a user and an accept button 314. Only after a user selects accept button 314 will user interface 145 revert to displaying window 216 and table 236 with a selected program button 250 with a changed graphical representation. In some examples, window 300 includes information relating to the vector associated with the selected one of program buttons 250. For example, window 300 may include a graphical representation of a heart, such as heart 301. Window 300 may further include a depiction of leads, such as leads 303, within heart 301. Attached to leads 303 may be electrodes, such as left ventricle electrodes 302, LVRing 1, LVRing 2, LVRing 3, and LVRing 4. RV electrode 304 may also be attached to leads 303. GUI 200 may additionally display a representation of the selected vector, such as by arrow 306. Arrow 306 may allow a user to easily visualize the electro-stimulation electrodes associated with the selected vector, for instance electrode LVRing2 and electrode RV in the example of FIG. 11.

GUI 200 may additionally display table 308 within window 300. Table 308 may include rows of electrodes that may act as cathodes during a delivery of electrical stimulation and columns of electrodes that may act as anodes during the delivery of electrical stimulation. Table 308 may additionally include graphical representations, such as first graphical representations 310, at each intersection of a row and a column. First graphical representations 310 may represent possible combinations of cathode electro-stimulation electrodes and anode electro-stimulation electrodes. In some examples, the same electro-stimulation electrode may not be both a cathode electro-stimulation electrode and an anode electrode stimulation electrode. Accordingly, table 308 may not contain any of first graphical representations 310 at intersections corresponding to the same electro-stimulation electrode, e.g. such as the intersection of electrode LVRing 2 and LVRing 2. In some examples, table 308 may additionally include a different graphical representation, such as second graphical representation 312, which corresponds to the selected vector. In the example of FIG. 11, GUI 200 displays table 308 with second graphical representation 312 at the intersection of electrode LVRing 2 and electrode RV, which corresponds to the vector selected in FIG. 10.

GUI 200 may additionally display selectable accept button 314 and selectable cancel button 318 within window 300. In some instances, the user may change or confirm a specific voltage and pulse width for medical device 101 to deliver electrical stimulation in this window. After reviewing the information displayed by GUI within window 300, a user may select accept button 314 to confirm the selected vector. Accordingly, in some examples, only after receiving a selection of accept button 314 will implantable medical device 101 or external assembly 140 program implantable medical device 101 to deliver electrical stimulation via the selected vector. In other instances, a user may select cancel button 318. After receiving a selection of cancel button 318, GUI 200 may cease displaying window 300 and revert to displaying window 216, such as in FIG. 10. In such examples, a user may then select a different vector and/or one of program buttons 250.

In some examples, GUI 200 may display one or more values in editable boxes representing a voltage amplitude and pulse width of electrical stimulation to be delivered via the programmed vector. For example, before selecting accept button 314, a user may edit the values displayed in such editable boxes. In some examples, GUI 200 may display predefined numbers in the editable boxes. In other examples, GUI 200 may display the determined capture threshold voltage (or a factor of the determined capture threshold voltage) for that vector in the editable box representing the voltage amplitude. In any example, a user may edit the values in either of the boxes (voltage amplitude or pulse width) before selecting accept button 314. In this manner, implantable medical device 101 and/or assembly 140 may receive voltage amplitude and pulse width parameters for use when delivering electrical stimulation via the programmed vector. In other examples, GUI 200 may display one or more editable boxes and prompt the user to enter or edit the voltage amplitude and pulse width parameters after receiving a selection of accept button 314 but before implantable medical device 101 is programmed to deliver electrical stimulation via the selected vector.

As described above with respect to other techniques of this disclosure, either implantable medical device 101, external assembly 140, or a combination of implantable medical device 101 and external assembly 140 may receive user input, for example the selections of the various vectors or buttons. Accordingly, device 101, assembly 140, or a combination, and more specifically, processor circuit 103 and/or processor circuit 143, may further process the user input and cause GUI to display window 300 and the above described features.

In some examples, system 100 may operate according to the techniques disclosed within U.S. Pub. No. 2012/0035685, "USER INTERFACE SYSTEM FOR USE WITH MULTIPOLAR PACING LEADS," to Saha et al., the entirety of which is incorporated herein by reference. For example, GUI 200 may include features disclosed within U.S. Pub. No. 2012/0035685. In some instances, GUI 200 may include features disclosed within U.S. Pub. No. 2012/0035685 in place of one or more features described within this disclosure.

Figure 12:
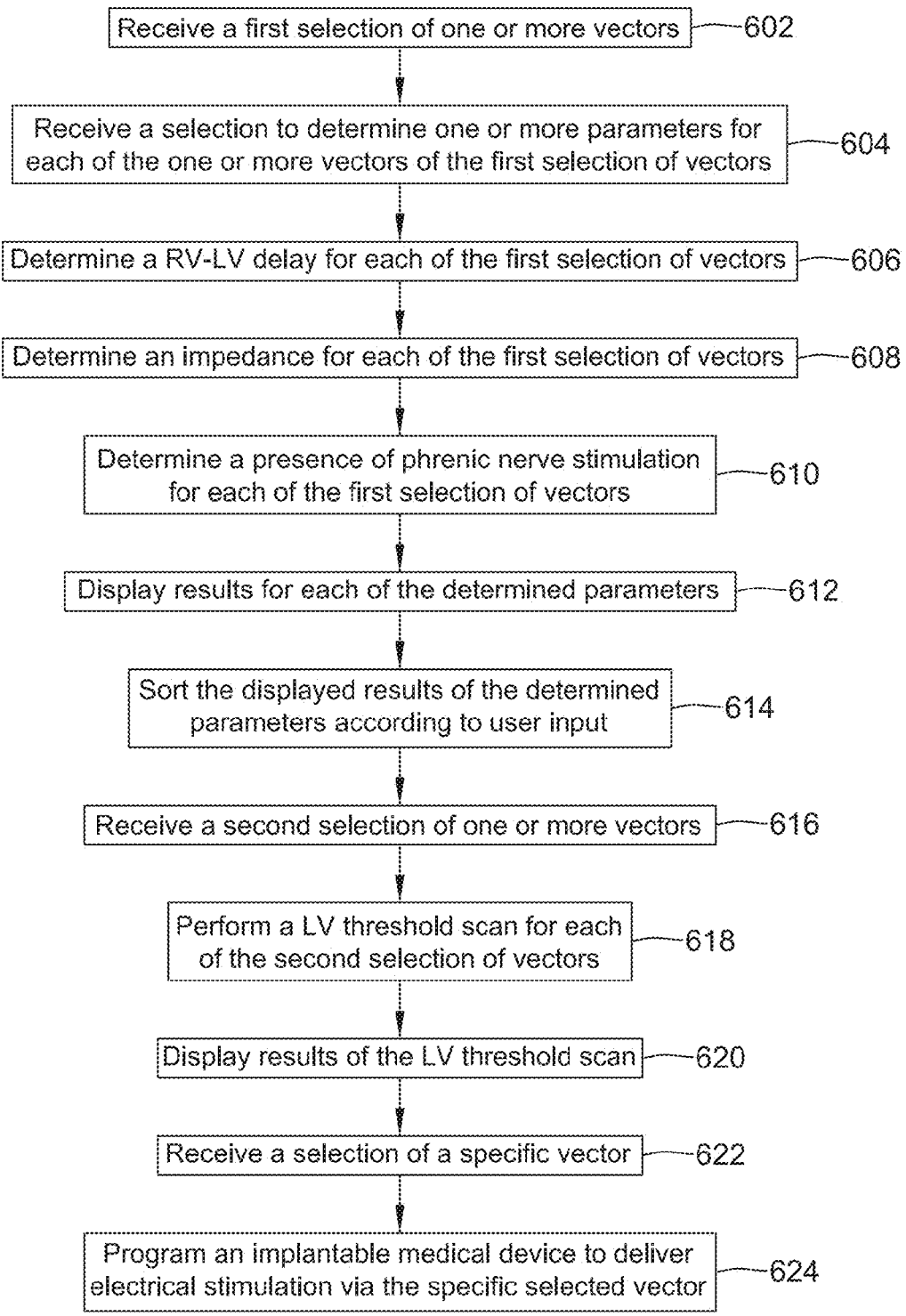
FIG. 12 shows a flow diagram of an illustrative method that may be implemented by an implantable medical device system such as the implantable medical system of FIG. 1.

FIGS. 12A-12B show a flow diagram of an illustrative method that may be implemented by an implantable medical device system such as the implantable medical device system of FIG. 1. Although the method of FIGS. 12A-12B will be described with respect to the implantable medical device system of FIG. 1, the method of FIGS. 12A-12B may be performed by any suitable medical device system.

A medical device system, such as system 100 of FIG. 1, including implantable medical device 101 and/or external assembly 140, may receive a first selection of one or more vectors 238, as shown at 602. In some examples, implantable medical device 101 and/or external assembly 140 may receive a specific selection of less than all vectors 238. In other examples, implantable medical device 101 and/or external assembly 140 may not receive a specific selection of any of vectors 238. In such examples, implantable medical device 101 and/or external assembly 140 may determine that not receiving a specific selection of any of vectors 238 is a selection of all of vectors 238.

Implantable medical device 101 and/or external assembly 140 may also receive a selection to determine one or more parameters for each of the one or more vectors of the first selection of vectors as shown at 604. For example, implantable medical device 101 and/or external assembly 140 may receive a selection of start AVS quickscan button 232. Upon receiving a selection of start AVS quickscan button 232, implantable medical device 101 and/or external assembly 140 may begin a scan of selected vectors. In some examples, as described previously, a scan may include determining RV-LV delays for each of the vectors (606), determining impedances for each of the vectors (608), and determining presence of phrenic nerve stimulation (610). In some examples, after receiving a selection of start AVS quickscan button 232, instead of determining each of the parameters in a single scan, implantable medical device 101 and/or external assembly 140 may perform two or more sequential scans in order to determine each of RV-LV delay, impedance, and presence of phrenic nerve stimulation parameters.

Implantable medical device 101 and/or external assembly 140 may additionally display results for each of the determined parameters (612), for example in corresponding columns of a table such as table 236. For example, implantable medical device 101 and/or external assembly 140 may cause user interface 145 to display a GUI 200 that includes table 236 that has the determined parameters. In some examples, implantable medical device 101 and/or external assembly 140 may display determinations of each parameter immediately after determining a parameter. In other examples, implantable medical device 101 and/or external assembly 140 may display determined parameters for each selected vector after determining a parameter for each of the selected vectors. For example, implantable medical device 101 and/or external assembly 140 may display an impedance for each selected vector after determining an impedance for each selected vector.

Implantable medical device 101 and/or external assembly 140 may additionally sort the displayed results of the determined parameters according to user input, as shown at 614. For example, implantable medical device 101 and/or external assembly 140 may receive a selection from a user to sort table 236 according to a first column. User interface 145 may receive user input, such as a selection, from a user and communicate the user input to processor circuit 143 and/or implantable medical device 101 and processor circuit 103. Implantable medical device 101 and/or processor circuit 103 may receive the user input from communication circuit 102, which in turn may have received the user input from communication circuit 142. Based on the user input, implantable medical device 101 and/or external assembly 140, and more specifically, processor circuit 103 and/or processor circuit 143, may cause GUI 200 to display table 236 with vectors 238 sorted according to the user input. For example, if the user input included a selection of the top cell of impedance column 242, implantable medical device 101 and/or external assembly 140 may cause GUI 200 to display table 236 with vectors 238 sorted according to their corresponding values in impedance column 242. In some examples, the user input may include selections of multiple columns. Accordingly, in such examples, GUI 200 may display vectors 238 sorted according to the multiple selected columns according to the order of column selection, in accordance with the techniques described above.

Implantable medical device 101 and/or external assembly 140 may additionally receive a second selection of one or more vectors, as shown at 616. In some examples, implantable medical device 101 and/or external assembly 140 may receive a specific selection of less than all vectors 238. In other examples, implantable medical device 101 and/or external assembly 140 may not receive a specific selection of any of vectors 238. In such examples, implantable medical device 101 and/or external assembly 140 may determine that not receiving a specific selection of any of vectors 238 is a selection of all of vectors 238.

Implantable medical device 101 and/or external assembly 140 may also perform a LV threshold scan for each of the second selection of vectors, as shown at 618. Implantable medical device 101 and/or external assembly 140 may then display results of the LV threshold scan such as in table 236, as shown at 620.

Implantable medical device 101 and/or external assembly 140 may further receive a selection of a specific vector, as shown at 622. For example, a user may input a selection of a specific vector into user interface 145. User interface 145 may then communicate the selected vector to implantable medical device 101 and processor circuit 103, such as through communication circuits 102 and 142, and/or external assembly 140 and processor circuit 143. Implantable medical device 101 and/or external assembly 140 may then program implantable medical device 101 to deliver electrical stimulation via the specific selected vector, as shown at 624.

Figure 13:
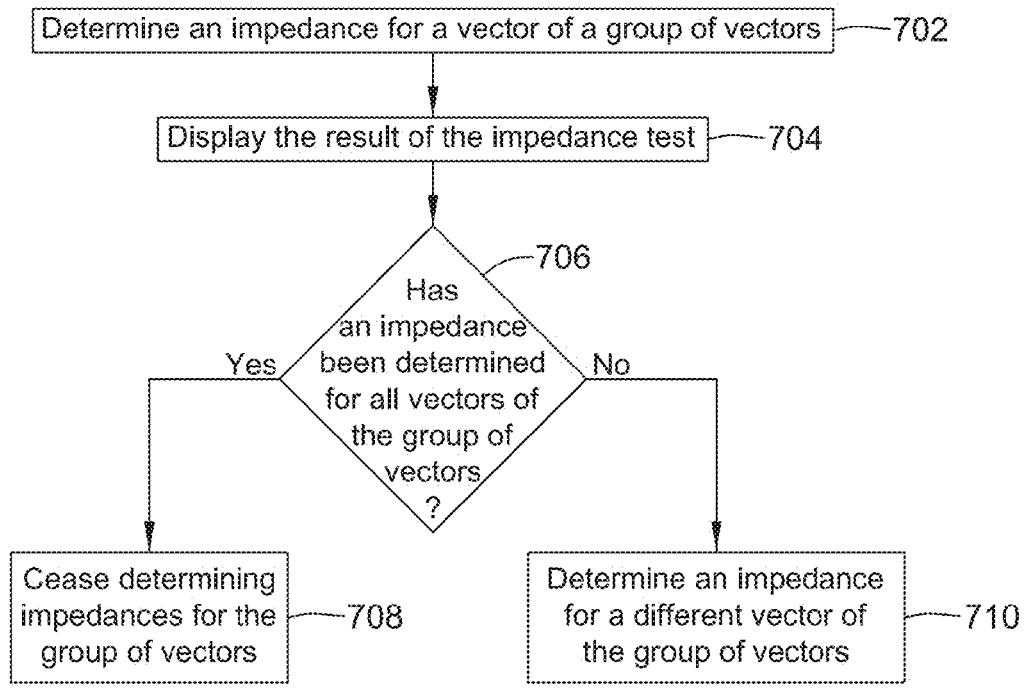
FIG. 13 is a flow diagram of another illustrative method of determining impedance that may be implemented by an implantable medical device system such as shown in FIG. 1.

FIG. 13 is a flow diagram of an illustrative method that may be implemented by an implantable medical device system such as shown in FIG. 1. Although the method of FIG. 13 will be described with respect to the medical device system of FIG. 1, the method of FIG. 13 may be performed by any suitable medical device system.

In some examples, implantable medical device 101 and/or external assembly 140 may determine an impedance for a vector of a group of vectors, as shown at 702. For example, a user may select one or more of vectors 238 to be grouped into a group of vectors. In some examples, the group of vectors is all of vectors 238, and in other examples the group of vectors is a set of less than all of vectors 238. In at least one example, processor circuit 103 and/or processor circuit 143 may cause implantable medical device 101 and/or external assembly 140, and more specifically, electro stimulation circuit 105 of implantable medical device 101 or an electro stimulation circuit of external assembly 140 (not shown in FIG. 1) to deliver electrical stimulation via a first electro-stimulation electrode of the vector. In some examples, the electrical stimulation may be a voltage pulse, and in other examples, the electrical stimulation may be a current pulse. In some examples, the electro stimulation may include a plurality of pulses.

Subsequently, implantable medical device 101 and/or external assembly 140 may measure one or more parameters of the vector. For example, implantable medical device 101 may use sensing circuit 106 to measure a current flow through the electro-stimulation electrodes of the vector or a voltage differential between the first electro-stimulation electrode and a second electro-stimulation electrode of the vector. In other examples, external assembly 140 may measure, for example with a sensing circuit (not shown in FIG. 1), a current flow through or a voltage differential between the first electro-stimulation electrode and a second electro-stimulation electrode of the vector. In still other examples, implantable medical device 101 and external assembly 140 may coordinate to measure a current flow through or a voltage differential between the first electro-stimulation electrode and a second electro-stimulation electrode of the vector.

Implantable medical device 101 and/or external assembly 140, using Ohm's Law, may then determine an impedance for the vector. For example, based on the measured current flow or voltage differential, along with features of the delivered voltage or current pulse, implantable medical device 101 and/or external assembly 140 may determine the impedance of the vector using Ohm's Law, $Z=V/I$.

Implantable medical device 101 and/or external assembly 140 may then display the result of the impedance test at user interface 145, as shown at 704. For example, implantable medical device 101 and/or external assembly 140 may cause GUI 200 to display table 236 with a value in the corresponding cell of impedance column 242 for the vector at user interface 145.

Implantable medical device 101 and/or external assembly 140 may then determine whether an impedance has been determined for all of the vectors of the group of vectors, as shown at 706. If an impedance has been determined for all of the vectors of the group of vectors, implantable medical device 101 and/or external assembly 140 may cease determining impedances for the group of vectors, as shown at 708. If an impedance has not been determined for all of the vectors of the group of vectors, implantable medical device 101 and/or external assembly 140 may determine an impedance for a different vector of the group of vectors, as shown at 710. For example, implantable medical device 101 and/or external assembly 140 may determine an impedance for a vector of the group of vectors for which implantable medical device 101 and/or external assembly 140 has not yet determined an impedance. In this manner, implantable medical device 101 and/or external assembly 140 may determine an impedance for each vector in the group of vectors.

Figure 14:
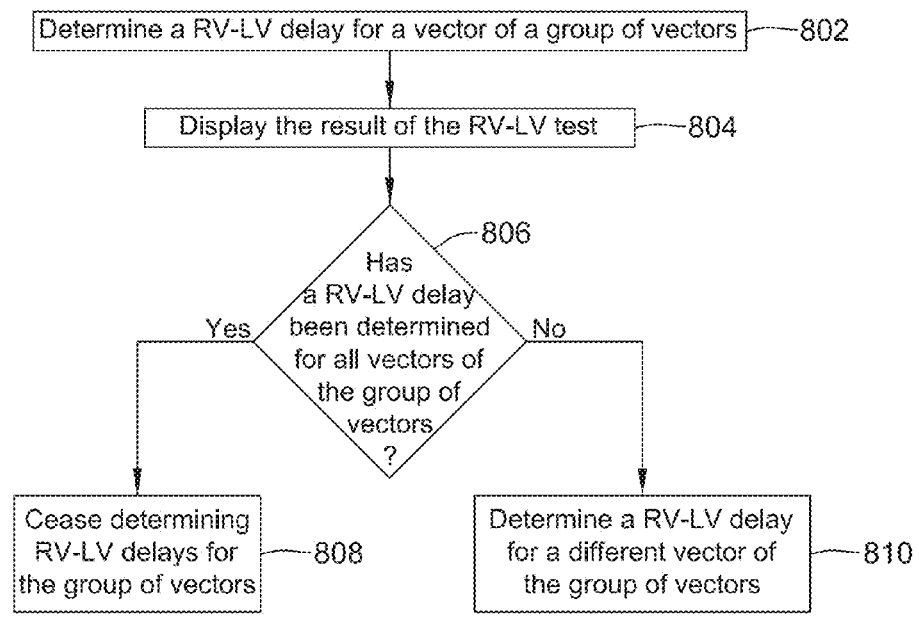
FIG. 14 is a flow diagram of an illustrative method of determining an RV-LV delay that may be implemented by an implantable medical device system such as shown in FIG. 1.

FIG. 14 is a flow diagram of an illustrative method that may be implemented by an implantable medical device system such as shown in FIG. 1. Although the method of FIG. 14 will be described with respect to the medical device system of FIG. 1, the method of FIG. 14 may be performed by any suitable medical device system.

In some examples, implantable medical device 101 and/or external assembly 140 may determine a RV-LV delay for a vector of a group of vectors, as shown at 802. In some examples, the group of vectors is all of vectors 238, and in other examples the group of vectors is a set of less than all of vectors 238. For example, a user may select one or more of vectors 238 to be grouped into the group of vectors. In at least one example, processor circuit 103 and/or processor circuit 143 may cause implantable medical device 101 and/or external assembly 140, and more specifically, electro stimulation circuit 105 of implantable medical device 101 or an electro stimulation circuit of external assembly 140 (not shown in FIG. 1) to deliver electrical stimulation via a first electro-stimulation electrode of the vector. In some examples, the electrical stimulation may be a voltage pulse, and in other examples, the electrical stimulation may be a current pulse. In some examples, the electro stimulation may include a plurality of pulses.

Subsequently, implantable medical device 101 and/or external assembly 140 may measure one or more parameters of the vector. For example, implantable medical device 101 may use sensing circuit 106 to measure an elapsed time between when implantable medical device 101 delivered electro stimulation to the first electro-stimulation electrode of the vector and when sensing circuit 106 detects the electro stimulation at a second electro-stimulation electrode of the vector. In other examples, external assembly 140 may measure, for example with a sensing circuit (not shown in FIG. 1), an elapsed time between when implantable medical device 101 delivered electro stimulation to the first electro-stimulation electrode of the vector and when sensing circuit 106 detects the electro stimulation at a second electro-stimulation electrode of the vector. In still other examples, implantable medical device 101 and external assembly 140 may coordinate to measure an elapsed time between when implantable medical device 101 delivered electro stimulation to the first electro-stimulation electrode of the vector and when sensing circuit 106 detects the electro stimulation at a second electro-stimulation electrode of the vector. This measured elapsed time may be the RV-LV delay for the vector. In other examples, implantable medical device 101 and/or external assembly 140, similarly to the process described above, may measure an elapsed time between delivering electrical stimulation to a first electro-stimulation electrode of the vector and a contraction of heart 115, with this elapsed time being the RV-LV delay for the vector.

Implantable medical device 101 and/or external assembly 140 may then display the result of the RV-LV delay test at user interface 145, as shown at 804. For example, implantable medical device 101 and/or external assembly 140 may cause GUI 200 to display table 236 with a value in the corresponding cell of RV-LV delay column 240 for the vector at user interface 145.

Implantable medical device 101 and/or external assembly 140 may then determine whether a RV-LV delay has been determined for all of the vectors of the group of vectors, as shown at 806. If a RV-LV delay has been determined for all of the vectors of the group of vectors, implantable medical device 101 and/or external assembly 140 may cease determining RV-LV delays for the group of vectors, as shown at 808. If a RV-LV delay has not been determined for all of the vectors of the group of vectors, implantable medical device 101 and/or external assembly 140 may determine a RV-LV delay for a different vector of the group of vectors, as shown at 810. For example, implantable medical device 101 and/or external assembly 140 may determine a RV-LV delay for a vector of the group of vectors for which implantable medical device 101 and/or external assembly 140 has not yet determined a RV-LV delay. In this manner, implantable medical device 101 and/or external assembly 140 may determine a RV-LV delay for each vector in the group of vectors.

Figure 15:
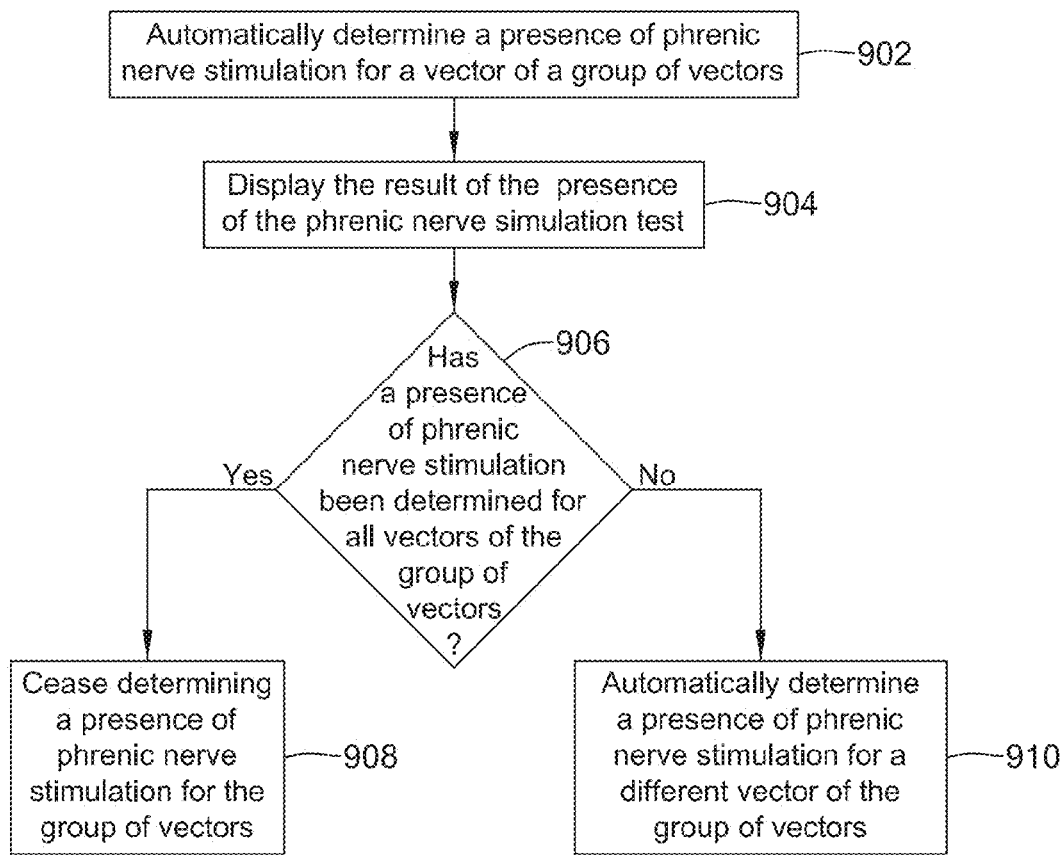
FIG. 15 is a flow diagram of an illustrative method of automatically determining the presence of phrenic nerve stimulation, which may be implemented by an implantable medical device system such as shown in FIG. 1.

FIG. 15 is a flow diagram of an illustrative method that may be implemented by an implantable medical device system such as shown in FIG. 1. Although the method of FIG. 15 will be described with respect to the medical device system of FIG. 1, the method of FIG. 15 may be performed by any suitable medical device system.

In some examples, implantable medical device 101 and/or external assembly 140 may automatically determine a presence of phrenic nerve stimulation for a vector of a group of vectors (902). In some examples, the group of vectors is all of vectors 238, and in other examples the group of vectors is a set of less than all of vectors 238. For example, a user may select one or more of vectors 238 to be grouped into the group of vectors. In at least one example, processor circuit 103 and/or processor circuit 143 may cause implantable medical device 101 and/or external assembly 140, and more specifically, electro stimulation circuit 105 of implantable medical device 101 or an electro stimulation circuit of external assembly 140 (not shown in FIG. 1) to deliver electrical stimulation via a first electro-stimulation electrode of the vector. In some examples, the electrical stimulation may be a voltage pulse, and in other examples, the electrical stimulation may be a current pulse. In some examples, the electro stimulation may include a plurality of pulses. In at least one example, implantable medical device 101 and/or external assembly 140 may deliver electrical stimulation at a first voltage amplitude. In some such examples, the first voltage amplitude may be a relatively high voltage amplitude (for example, 6 V, 7 V, 7.5 V, 8 V, etc.). Additionally in some examples, the first voltage amplitude is a maximum voltage that implantable medical device 101 and/or external assembly 140 is capable of delivering via the vector.

Subsequently, implantable medical device 101 and/or external assembly 140 may measure one or more parameters of the vector. For example, implantable medical device 101 may use sensing circuit 106 (sometimes including an accelerometer) to measure an activation of a phrenic nerve. In other examples, external assembly 140 may measure, for example with a sensing circuit (not shown in FIG. 1), an activation of the phrenic nerve. In still other examples, implantable medical device 101 and external assembly 140 may coordinate to measure an activation of the phrenic nerve. In some cases, a user (e.g. physician) may enter via the user interface 145 whether phrenic nerve stimulation was observed during the particular vector.

Implantable medical device 101 and/or external assembly 140 may then display the result of the phrenic nerve stimulation test at user interface 145, as shown at 904. For example, implantable medical device 101 and/or external assembly 140 may cause GUI 200 to display table 236 with a value in the corresponding cell of PS threshold column 244 for the vector at user interface 145.

Implantable medical device 101 and/or external assembly 140 may then determine whether presence of phrenic nerve stimulation has been determined for all of the vectors of the group of vectors, as shown at 906. If a presence of phrenic nerve stimulation has been determined for all of the vectors of the group of vectors, implantable medical device 101 and/or external assembly 140 may cease determining presence of phrenic nerve stimulation for the group of vectors, as shown at 908. If presence of phrenic nerve stimulation has not yet been determined for all of the vectors of the group of vectors, implantable medical device 101 and/or external assembly 140 may continue to determine presence of phrenic nerve stimulation for a different vector of the group of vectors, as shown at 910. For example, implantable medical device 101 and/or external assembly 140 may determine presence of phrenic nerve stimulation for a vector of the group of vectors for which implantable medical device 101 and/or external assembly 140 has not yet determined presence of phrenic nerve stimulation. In this manner, implantable medical device 101 and/or external assembly 140 may determine a presence of phrenic nerve stimulation for each vector in the group of vectors.

Figure 16:
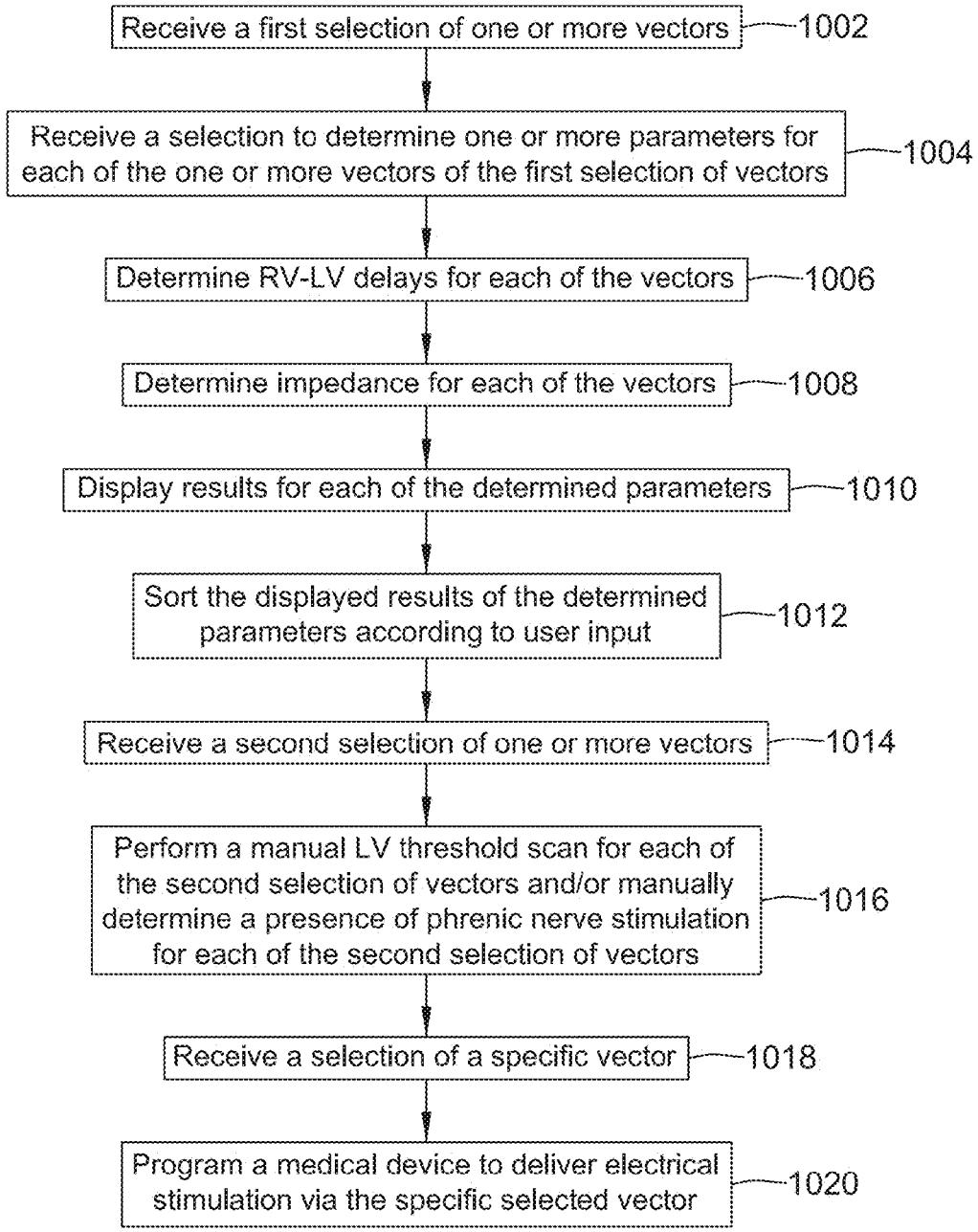
FIG. 16 is a flow diagram of another illustrative method that may be implemented by an implantable medical device system such as the implantable medical system of FIG. 1.

FIG. 16 is a flow diagram of an illustrative method that may be implemented by an implantable medical device system such as shown in FIG. 1. Although the method of FIG. 16 will be described with respect to the medical device system of FIG. 1, the method of FIG. 16 may be performed by any suitable medical device system.

A medical device system, such as system 100 of FIG. 1, including implantable medical device 101 and/or external assembly 140, may receive a first selection of one or more vectors 238, as shown at 1002. In some examples, implantable medical device 101 and/or external assembly 140 may receive a specific selection of less than all vectors 238.

In other examples, implantable medical device 101 and/or external assembly 140 may not receive a specific selection of any of vectors 238. In such examples, implantable medical device 101 and/or external assembly 140 may determine that not receiving a specific selection of any of vectors 238 is a selection of all of vectors 238. Implantable medical device 101 and/or external assembly 140 may also receive a selection to determine one or more parameters for each of the one or more vectors of the first selection of vectors, as shown at 1004. For example, implantable medical device 101 and/or external assembly 140 may receive a selection of a start AVS quickscan button 232. Upon receiving a selection of start AVS quickscan button 232, implantable medical device 101 and/or external assembly 140 may begin a scan of selected vectors. In some examples, as described previously, a scan may include determining RV-LV delays for each of the vectors (1006) and determining impedances for each of the vectors (1008). In some examples, after receiving a selection of start AVS quickscan button 232, instead of determining each of the parameters in a single scan, implantable medical device 101 and/or external assembly 140 may perform two (or more) sequential scans in order to determine each of RV-LV delay and impedance parameters.

Implantable medical device 101 and/or external assembly 140 may additionally display results for each of the determined parameters, as shown at 1010, for example in corresponding columns of table 236. For example, implantable medical device 101 and/or external assembly 140 may cause user interface 145 to display a table 236 that includes the determined parameters. In some examples, implantable medical device 101 and/or external assembly 140 may display determinations of each parameter immediately after determining a parameter. In other examples, implantable medical device 101 and/or external assembly 140 may display determined parameters for each selected vector after determining a parameter for each of the selected vectors. For example, implantable medical device 101 and/or external assembly 140 may display an impedance for each selected vector after determining an impedance for each selected vector.

Implantable medical device 101 and/or external assembly 140 may additionally sort the displayed results of the determined parameters according to user input, as shown at 1012. For example, implantable medical device 101 and/or external assembly 140 may receive a selection from a user to sort table 236 according to a first column. User interface 145 may receive user input, such as a selection, from a user and communicate the user input to processor circuit 143 and/or implantable medical device 101 and processor circuit 103. Implantable medical device 101 and/or processor circuit 103 may receive the user input from communication circuit 102, which in turn may have received the user input from communication circuit 142. Based on the user input, implantable medical device 101 and/or external assembly 140, and more specifically, processor circuit 103 and/or processor circuit 143, may cause GUI 200 to display table 236 with vectors 238 sorted according to the user input. For example, if the user input included a selection of the top cell of impedance column 242, implantable medical device 101 and/or external assembly 140 may cause GUI 200 to display table 236 with vectors 238 sorted according to their corresponding values in impedance column 242. In some examples, the user input may include selections of multiple columns. Accordingly, in such examples, GUI 200 may display vectors 238 sorted according to the multiple selected columns according to the order of selection, such as in accordance with the techniques described above.

Implantable medical device 101 and/or external assembly 140 may additionally receive a second selection of one or more vectors, as shown at 1014. In some examples, implantable medical device 101 and/or external assembly 140 may receive a specific selection of less than all vectors 238. In other examples, implantable medical device 101 and/or external assembly 140 may not receive a specific selection of any of vectors 238. In such examples, implantable medical device 101 and/or external assembly 140 may determine that not receiving a specific selection of any of vectors 238 is a selection of all of vectors 238.

Implantable medical device 101 and/or external assembly 140 may also perform a manual LV threshold scan for each of the second selection of vectors and/or manually determine a presence of phrenic nerve stimulation for each of the second selection of vectors, as shown at 1016. For example, implantable medical device 101 and/or external assembly 140 may perform the manual LV threshold scan for each of the second selection of vectors and/or manually determine a presence of phrenic nerve stimulation for each of the second selection of vectors, such as in accordance with the illustrative method of FIG. 17 described below.

Implantable medical device 101 and/or external assembly 140 may further receive a selection of a specific vector, as shown at 1018. For example, a user may input a selection of a specific vector into user interface 145. User interface 145 may then communicate the selected vector to implantable medical device 101 and processor circuit 103, such as through communication circuits 102 and 142, and/or external assembly 140 and processor circuit 143. Implantable medical device 101 and/or external assembly 140 may then program implantable medical device 101 to deliver electrical stimulation via the specific selected vector, as shown at 1020.

Figure 17:
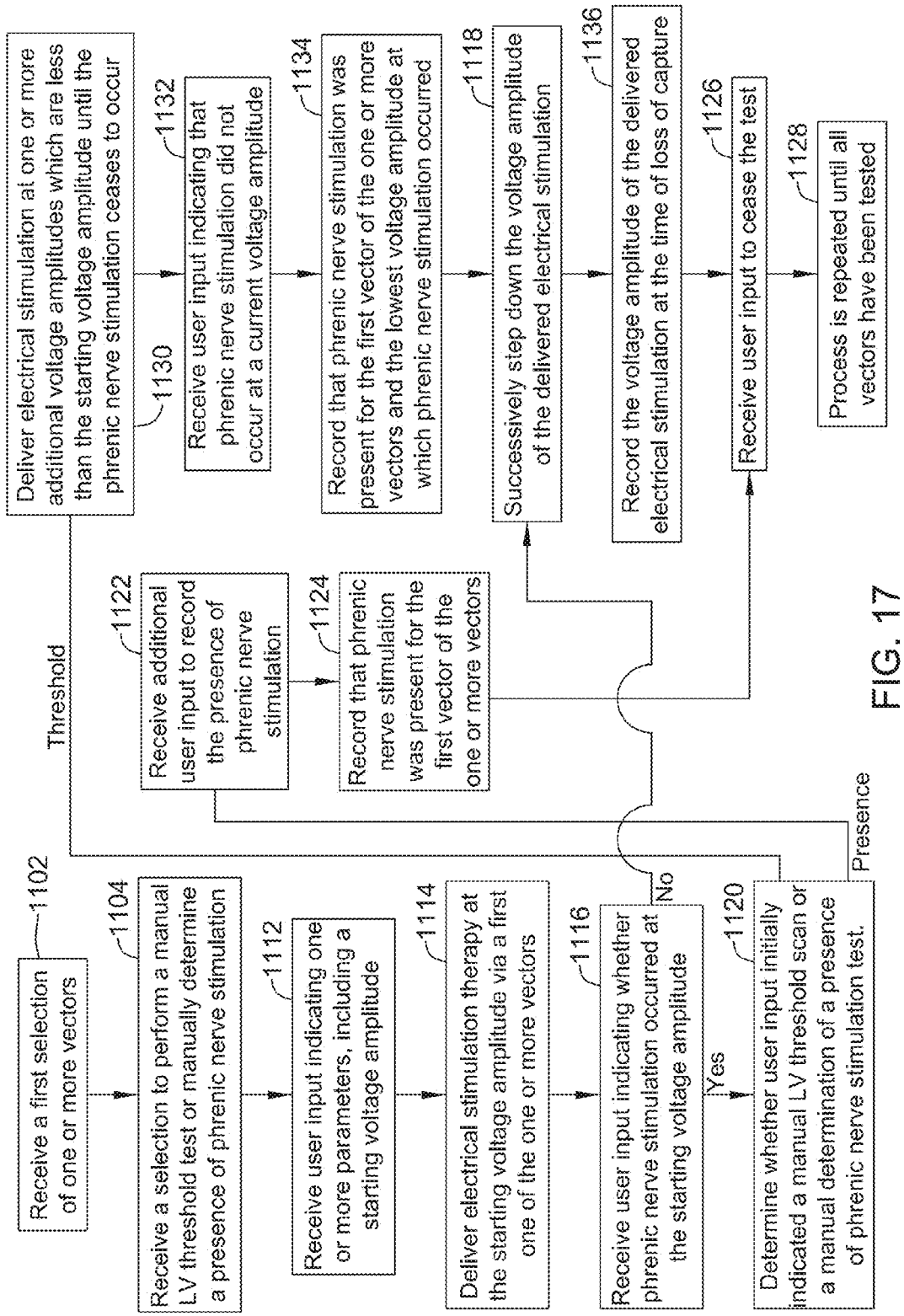
FIG. 17 is a flow diagram of an illustrative method for determining a plurality of metrics for vectors, which may be implemented by an implantable medical device system such as the implantable medical system of FIG. 1.

FIG. 17 is a flow diagram of an illustrative method that may be implemented by an implantable medical device system such as shown in FIG. 1. Although the method of FIG. 17 will be described with respect to the medical device system of FIG. 1, the method of FIG. 17 may be performed by any suitable medical device system.

A medical device system, such as system 100 of FIG. 1, including implantable medical device 101 and/or external assembly 140, may receive a selection of one or more vectors 238, as shown at 1102. In some examples, implantable medical device 101 and/or external assembly 140 may receive a specific selection of less than all vectors 238. In other examples, implantable medical device 101 and/or external assembly 140 may not receive a specific selection of any of vectors 238. In such examples, implantable medical device 101 and/or external assembly 140 may determine that not receiving a specific selection of any of vectors 238 is a selection of all of vectors 238.

Implantable medical device 101 and/or external assembly 140 may also receive a selection to perform a manual LV threshold scan for each of the one or more vectors or to manually determine a presence of phrenic nerve stimulation for each of the one or more vectors, as shown at 1104. For example, implantable medical device 101 and/or external assembly 140 may receive a selection of a button, such as start AVS quickscan button 232 or start LV threshold search button 252. In some examples, after receiving a selection of start LV threshold search button 252, implantable medical device 101 and/or external assembly 140 may cause GUI 200 to display an option for a user to select either a manual LV threshold scan or a manual determination of a presence of phrenic nerve stimulation test.

Upon receiving a selection of either option—where a user selects a manual LV threshold scan or where a user selects a manual determination of a presence of phrenic nerve stimulation test—implantable medical device 101 and/or external assembly 140 may additionally receive user input indicating one or more starting parameters, including a starting voltage amplitude, as shown at 1112. For example, a user may input into user interface 145 a starting voltage amplitude for the test, where the starting voltage amplitude is the voltage amplitude at which implantable medical device 101 and/or external assembly 140 may begin to deliver electrical stimulation to heart 115 during the test. Next, implantable medical device 101 and/or external assembly 140 may deliver electrical stimulation therapy, for example electrical stimulation pulses, at the starting voltage amplitude via a first one of the one or more vectors, as shown at 1114.

Next, implantable medical device 101 and/or external assembly 140 may receive additional user input, for example from a physician or a patient, indicating whether phrenic nerve stimulation occurred at the starting voltage amplitude, as shown at 1116. If the user input indicated that phrenic nerve stimulation did not occur, implantable medical device 101 and/or external assembly 140 may successively step down the voltage amplitude of the delivered electrical stimulation as shown at 1118. For example, implantable medical device 101 and/or external assembly 140 may deliver electrical stimulation at a second voltage amplitude that is less than the starting voltage amplitude. In some examples, the decrease in voltage amplitude may be 0.25 V, 0.5 V, 0.75 V, 1 V, or any other suitable voltage increment. Implantable medical device 101 and/or external assembly 140 may continue to step down the voltage amplitude of the delivered electrical stimulation in such a manner until a loss of capture of heart 115 is detected. In some examples, implantable medical device 101 and/or external assembly 140 receive input or determine when the electrical stimulation failed to capture heart 115, and implantable medical device 101 and/or external assembly 140 may then record the voltage amplitude of the delivered electrical stimulation at the time of loss of capture (1136). Additionally in some examples, implantable medical device 101 and/or external assembly 140 may receive input or determine that the implantable medical device 101 and/or external assembly 140 should cease the test, as shown at 1126.

In one example, if the user input indicated that phrenic nerve stimulation did occur, implantable medical device 101 and/or external assembly 140 may determine whether user input initially indicated a manual LV threshold scan or a manual determination of a presence of phrenic nerve stimulation test, as shown at 1120. If the user input initially indicated a manual determination of a presence of phrenic nerve stimulation test (PRESENCE branch at 1120), implantable medical device 101 and/or external assembly 140 may receive additional user input to record the presence of phrenic nerve stimulation, as shown at 1122. Implantable medical device 101 and/or external assembly 140 may then record that phrenic nerve stimulation was present for the first vector of the one or more vectors, as shown at 1124. In some examples, implantable medical device 101 and/or external assembly 140 may additionally record the voltage amplitude at which the phrenic nerve stimulation occurred. Implantable medical device 101 and/or external assembly 140 may also display, in the corresponding row of PS threshold column 244 of table 236, a value indicating that phrenic nerve stimulation was present for the first vector of the one or more vectors.

If the user input initially indicated a manual LV threshold scan (THRESHOLD branch of 1120), implantable medical device 101 and/or external assembly 140 may deliver electrical stimulation at one or more additional voltage amplitudes which are less than the starting voltage amplitude until the phrenic nerve stimulation ceases to occur, as shown at 1130. At the voltage amplitude where phrenic nerve stimulation ceases to occur, implantable medical device 101 and/or external assembly 140 may receive user input indicating that phrenic nerve stimulation did not occur at the current voltage amplitude, as shown at 1132. Implantable medical device 101 and/or external assembly 140 may then record that phrenic nerve stimulation was present for the first vector of the one or more vectors and the lowest voltage amplitude at which phrenic nerve stimulation occurred, as shown at 1134. Implantable medical device 101 and/or external assembly 140 may also display, in the corresponding row of PS threshold column 244 of table 236, a value indicating that phrenic nerve stimulation was present, and the lowest voltage amplitude at which phrenic nerve stimulation was present, for the first vector of the one or more vectors. After recording that phrenic nerve stimulation occurred and the lowest voltage amplitude at which phrenic nerve stimulation occurred, implantable medical device 101 and/or external assembly 140 may additionally successively step down the voltage amplitude of the delivered electrical stimulation, as shown at 1118. Implantable medical device 101 and/or external assembly 140 may continue to step down the voltage amplitude of the delivered electrical stimulation in such a manner until a loss of capture of heart 115 is detected. In some examples, implantable medical device 101 and/or external assembly 140 may receive user input indicating when the electrical stimulation failed to capture heart 115, and implantable medical device 101 and/or external assembly 140 may then record the voltage amplitude of the delivered electrical stimulation at the time of loss of capture, as shown at 1136. Additionally in some examples, implantable medical device 101 and/or external assembly 140 may receive user input directing implantable medical device 101 and/or external assembly 140 to cease the test, as shown at 1126.

After receiving an indication to cease the test (1126), implantable medical device 101 and/or external assembly 140 may repeat the above described process, starting at 1112, for a second one of the one or more vectors. Such a process may be repeated for each vector of the one or more vectors. In some examples, after receiving an indication to cease the test as shown at 1126, implantable medical device 101 and/or external assembly 140 may repeat the above described process starting at 1112, where implantable medical device 101 and/or external assembly 140 may receive an indication of a second one of the one or more vectors. In some cases, this process may be repeated until all of the vectors of a group of vectors have been tested.

Figure 18:
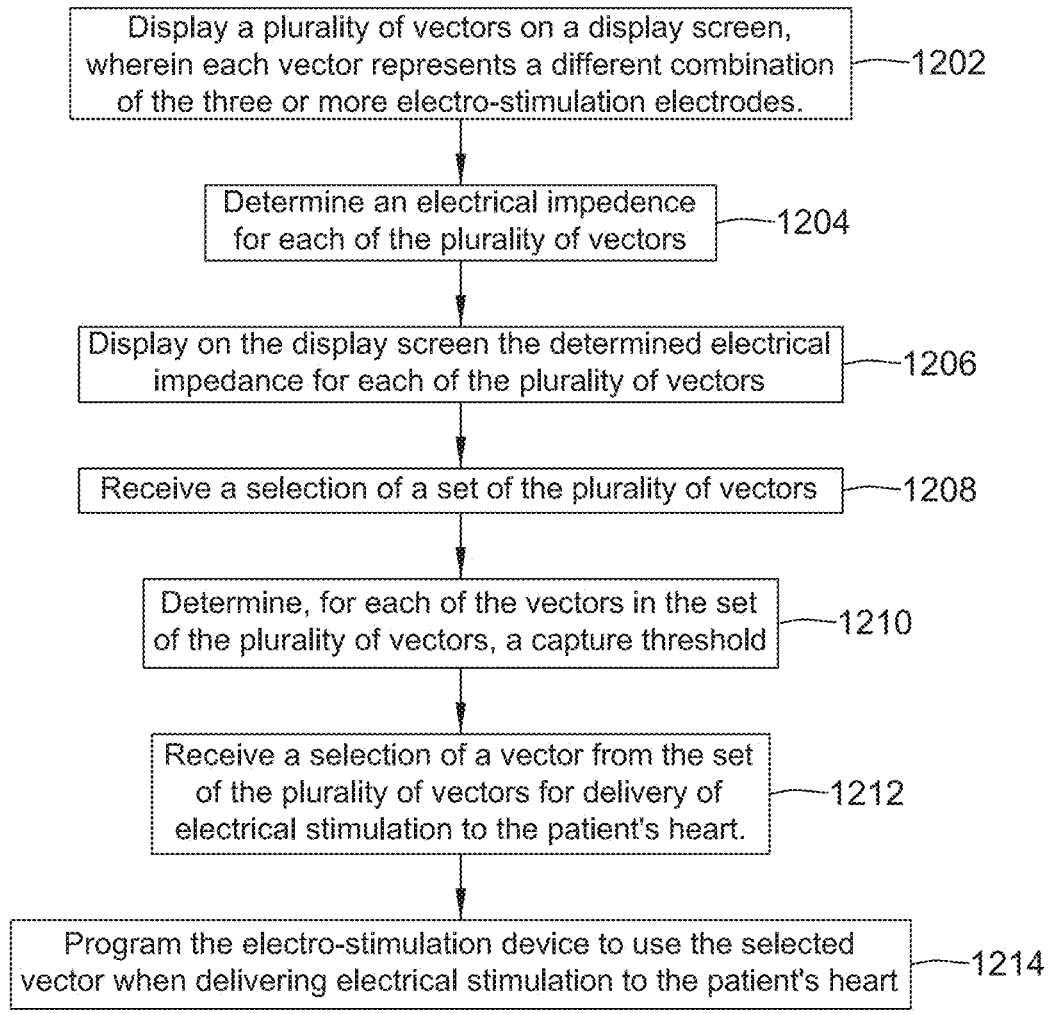
FIG. 18 is a flow diagram of another illustrative method that may be implemented by an implantable medical device system such as the implantable medical system of FIG. 1.

FIG. 18 is a flow diagram of a method that may be implemented by an implantable medical device system such as shown in FIG. 1. Although the method of FIG. 18 will be described with respect to the medical device system of FIG. 1, the method of FIG. 18 may be performed by any suitable medical device system.

A medical device system, such as system 100 of FIG. 1, including implantable medical device 101 and/or external assembly 140, may display a plurality of vectors on a display screen, wherein each vector represents a different combination of three or more electro-stimulation electrodes (1202). For example, implantable medical device 101 and/or external assembly 140 may cause GUI 200 to display vectors 238 at user interface 145. Implantable medical device 101 and/or external assembly 140 may additionally determine an electrical impedance for each of the plurality of vectors, as shown at 1204. For example, implantable medical device 101 and/or external assembly 140 may deliver a voltage pulse or a current pulse to a first one of the electro-stimulation electrodes of each of the vectors. Implantable medical device 101 and/or external assembly 140 may additionally measure one or more parameters of the vector, for example the current flowing through the two electro-stimulation electrodes of each vector or the voltage differential across the two electro-stimulation electrodes of the vector. Based on the measure delivered pulses and the measured parameters, in conjunction with Ohm's Law, implantable medical device 101 and/or external assembly 140 may determine the impedance of each vector.

Implantable medical device 101 and/or external assembly 140 may then display on the display screen the determined electrical impedance for each of the plurality of vectors, as shown at 1206. Next, implantable medical device 101 and/or external assembly 140 may receive a selection of a set of the plurality of vectors, as shown at 1208. For example, a user may enter user input into user interface 145, wherein the user input indicates a selection of a set of the plurality of vectors. User interface 145 may communicate the user input to other circuitry of external assembly 140, for example, processor circuit 143. User interface 145 may alternatively or additionally communicate the input to implantable medical device 101. For example, user interface 145 may communicate the user input to communication circuit 142 and communication circuit 142 may communicate the user input to communication circuit 102, which may, in turn, communicate the user input to other circuitry within implantable medical device 101.

Implantable medical device 101 and/or external assembly 140 may then determine, for each of the vectors in the set of the plurality of vectors, a capture threshold as shown at 1210. For example, implantable medical device 101 and/or external assembly 140 may deliver electrical stimulation at a first voltage amplitude to each vector and determine whether the electrical stimulation resulted in a capture of heart 115. If the electrical stimulation did result in a capture of heart 115, implantable medical device 101 and/or external assembly 140 may step down the voltage amplitude of the delivered electrical stimulation and again check to see if the delivered electrical stimulation capture heart 115. Implantable medical device 101 and/or external assembly 140 may repeat this process until implantable medical device 101 and/or external assembly 140 determines that the delivered electrical stimulation did not capture heart 115. The lowest voltage amplitude at which the delivered electrical stimulation captured heart 115 may be the capture threshold.

Implantable medical device 101 and/or external assembly 140 may then receive a selection of a vector from the set of the plurality of vectors for delivery of electrical stimulation to the patient's heart, as shown at 1212. For example, a user may enter user input into user interface 145, wherein the user input indicates a selection of a vector from the set of the plurality of vectors. User interface 145 may communicate the user input to other circuitry of external assembly 140, for example, processor circuit 143. User interface 145 may alternatively or additionally communicate the input to implantable medical device 101. For example, user interface 145 may communicate the user input to communication circuit 142 and communication circuit 142 may communicate the user input to communication circuit 102, which may, in turn, communicate the user input to other circuitry within implantable medical device 101.

Implantable medical device 101 and/or external assembly 140 may then program the electro-stimulation device to use the selected vector when delivering electrical stimulation to the patient's heart, as shown at 1214. For example, implantable medical device 101 and/or external assembly 140 may store the selected vector into memory circuit 104 of implantable medical device 101. Additionally, when delivering electrical stimulation, processor circuit 103 may cause electro-stimulation circuit 105 to only deliver electrical stimulation via the selected vector that is stored in memory circuit 104.

Figure 19:
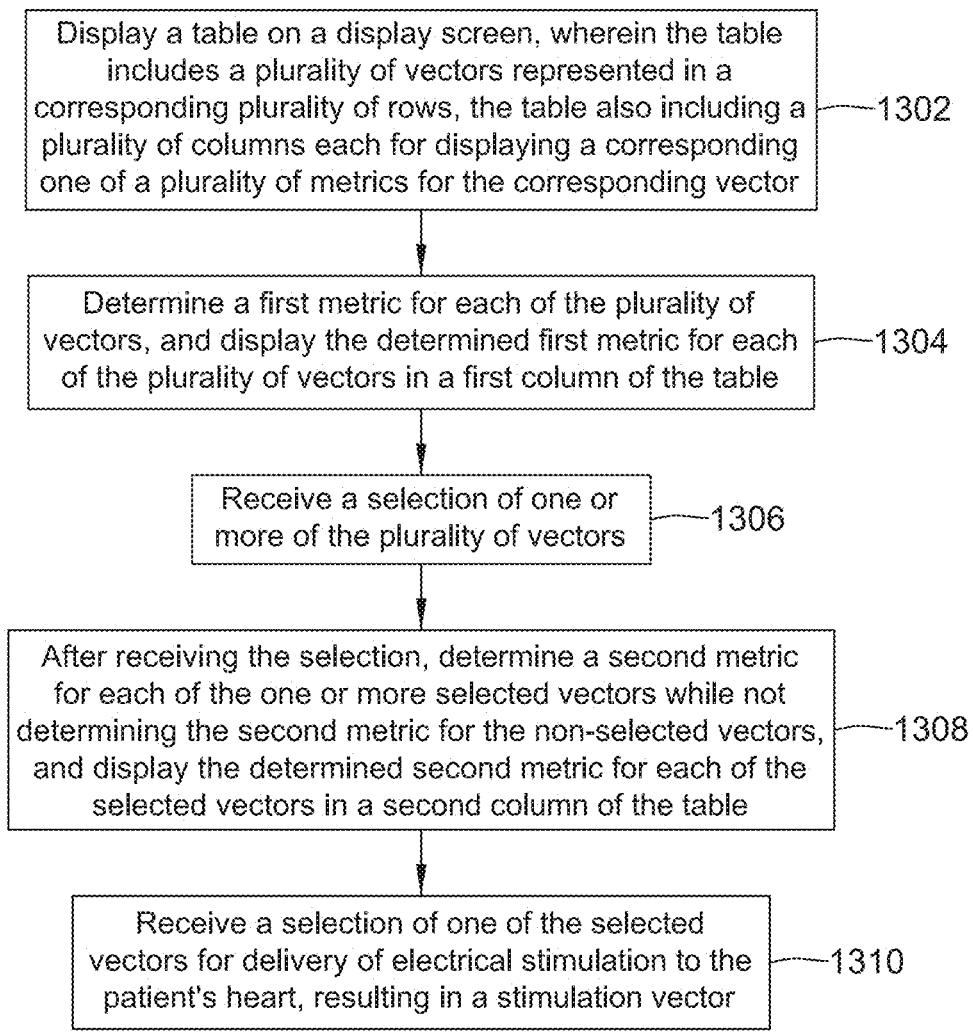
FIG. 19 is a flow diagram of another illustrative method that may be implemented by an implantable medical device system such as the implantable medical system of FIG. 1.

FIG. 19 is a flow diagram of a method that may be implemented by an implantable medical device system such as shown in FIG. 1. Although the method of FIG. 19 will be described with respect to the medical device system of FIG. 1, the method of FIG. 19 may be performed by any suitable medical device system.

A medical device system, such as system 100 of FIG. 1, including implantable medical device 101 and/or external assembly 140, may display a table on a display screen, wherein the table includes a plurality of vectors represented in a corresponding plurality of rows, the table also including a plurality of columns each for displaying a corresponding one of a plurality of metrics for the corresponding vector, as shown at 1302. For example, implantable medical device 101 and/or external assembly 140 may cause GUI 200 to display table 236 including vectors 238 and each of RV-LV delay column 240, impedance column 242, PS threshold column 244, and LV threshold column 246.

Implantable medical device 101 and/or external assembly 140 may also determine a first metric for each of the plurality of vectors, and display the determined first metric for each of the plurality of vectors in a first column of the table, as shown at 1304. For example, implantable medical device 101 and/or external assembly 140 may determine any of the RV-LV delay, impedance, or PS threshold metrics in accordance with any of the techniques described herein. Implantable medical device 101 and/or external assembly 140 may further cause GUI 200 to display values of the determined metric in table 236 under a corresponding column.

Implantable medical device 101 and/or external assembly 140 may additionally receive a selection of one or more of the plurality of vectors, as shown at 1306. For example, a user may enter user input into user interface 145, wherein the user input indicates a selection of one or more of the plurality of vectors. User interface 145 may communicate the user input to other circuitry of external assembly 140, for example, processor circuit 143. User interface 145 may alternatively or additionally communicate the input to implantable medical device 101. For example, user interface 145 may communicate the user input to communication circuit 142 and communication circuit 142 may communicate the user input to communication circuit 102, which may, in turn, communicate the user input to other circuitry within implantable medical device 101.

Implantable medical device 101 and/or external assembly 140 may further, after receiving the selection, determine a second metric for each of the one or more selected vectors while not determining the second metric for the non-selected vectors, and display the determined second metric for each of the selected vectors in a second column of the table, as shown at 1308. For example, implantable medical device 101 and/or external assembly 140 may determine any of the RV-LV delay, impedance, or PS threshold metrics not already determined, in accordance with any of the techniques described herein. Implantable medical device 101 and/or external assembly 140 may also only determine the second metric for the selected vectors. Implantable medical device 101 and/or external assembly 140 may further cause GUI 200 to display values of the determined second metric in table 236 under a corresponding column.

Implantable medical device 101 and/or external assembly 140 may ultimately receive a selection of one of the selected vectors for delivery of electrical stimulation to the patient's heart, resulting in a stimulation vector, as shown at 1310. For example, a user may enter user input into user interface 145, wherein the user input indicates a selection of one of the selected vectors. User interface 145 may communicate the user input to other circuitry of external assembly 140, for example, processor circuit 143. User interface 145 may alternatively or additionally communicate the input to implantable medical device 101. For example, user interface 145 may communicate the user input to communication circuit 142 and communication circuit 142 may communicate the user input to communication circuit 102, which may, in turn, communicate the user input to other circuitry within implantable medical device 101. In some examples, implantable medical device 101 and/or external assembly 140 may program implantable medical device 101 to use the selected vector when delivering electrical stimulation to heart 115. For example, implantable medical device 101 and/or external assembly 140 may store the selected vector into memory circuit 104 of implantable medical device 101. Additionally, when delivering electrical stimulation, processor circuit 103 may cause electro-stimulation circuit 105 to only deliver electrical stimulation via the stimulation vector that is stored in memory circuit 104.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of facilitating selection of a vector for delivering electrical stimulation to a patient's heart via an electro-stimulation device having three or more electro-stimulation electrodes using a device-based cardiac capture threshold test, the method comprising:
   displaying a plurality of vectors on a display screen, wherein each vector represents a different combination of the three or more electro-stimulation electrodes;
   measuring an electrical pacing impedance for each of the plurality of vectors using the electro-stimulation electrodes;
   displaying on the display screen the measured electrical pacing impedance for each of the plurality of vectors;
   receiving a selection of a set of the plurality of vectors as a selected first sub-set of the plurality of vectors in response to the displaying on the display screen the measured electrical pacing impedance for each of the plurality of vectors;
   determining a capture threshold for each of the vectors of the first subset of the plurality of vectors;
   displaying on the display screen the determined capture threshold for each of the vectors of the first subset of the plurality of vectors;
   receiving a further selection of a vector from the received first subset of the plurality of vectors, in response to the displaying on the display screen the determined capture threshold, for delivery of electrical stimulation to the patient's heart; and
   programming the electro-stimulation device to use the selected vector when delivering electrical stimulation to the patient's heart.

2. The method of claim 1, wherein after displaying the plurality of vectors on the display screen but before receiving the selection of the set of the plurality of vectors, the method further comprises:
   determining an electrical delay for each of the plurality of vectors; and
   displaying on the display screen the determined electrical delay and the measured electrical impedance for each of the plurality of vectors.

3. The method of claim 2, further comprising displaying on the display screen the determined electrical delay and the measured electrical impedance for each of the plurality of vectors in a table format, wherein the plurality of vectors are each represented in a row, and the determined electrical delay and the measured electrical impedance are represented in columns.

4. The method of claim 3, further comprising:
selecting a first column; and
sorting the table by the selected first column.

5. The method of claim 4, further comprising:
selecting a second column after selecting the first column; and
sorting the table by the first column, and then if duplicate entries exist in the first column, sorting the duplicate entries by the second column.

6. The method of claim 4, further comprising:
selecting one or more rows from the table that is sorted by the first column;
selecting a second column; and
sorting the selected rows by the selected second column.

7. The method of claim 2, wherein determining an electrical delay includes determining an RV-LV delay for each of the plurality of vectors,
wherein displaying on the display screen the measured electrical pacing impedance for each of the plurality of vectors includes displaying the determined RV-LV delay for each of the plurality of vectors, and
wherein receiving the selection of the set of the plurality of vectors as the selected first sub-set of the plurality of vectors in response to the displaying on the display screen
the measured electrical pacing impedance for each of the plurality of vectors and the determined RV-LV delay for each of the plurality of vectors.

8. The method of claim 1, further comprising determining a phrenic nerve stimulation value for the first sub-set of the plurality of vectors, and displaying on the display screen the determined phrenic nerve stimulation value for each of the vectors.

9. The method of claim 8, further comprising sorting the plurality of vectors based on the measured pacing impedance and the determined phrenic nerve stimulation value.

10. The method of claim 1, wherein the selected subsets of the plurality of vectors include less than all of the plurality of vectors.

11. A system for facilitating selection of at least one vector for delivering electrical stimulation to a chamber of a patient's heart via an electro-stimulation device, the system comprising:
a display screen; and
a controller configured to initiate capture threshold testing including:
present, at the display screen, a plurality of vectors, wherein each vector represents a different combination of electro-stimulation electrodes used to deliver the electrical stimulation;
measure an electrical pacing impedance for each of the plurality of vectors using the electro-stimulation electrodes;
present, at the display screen, the measured electrical pacing impedance for each of the plurality of vectors;
receive a selection of a set of vectors from the plurality of vectors as a selected first subset of the plurality of vectors in response to the presenting on the display screen the measured electrical pacing impedance for each of the plurality of vectors;
determine a capture threshold for each of the vectors of the first subset of the plurality of vectors;
present, at the display screen, the determined capture threshold for each of the vectors of the first subset of the plurality of vectors;
receive a further selection of a vector from the received first subset of the plurality of vectors, in response to the presented determined capture threshold, for delivery of electrical stimulation to the patient's heart; and
program the electro-stimulation device to use the selected vector when delivering electrical stimulation to the patient's heart.

12. The system of claim 11, wherein the controller is further configured to:
determine an electrical delay for the plurality of vectors;
present, at the display screen, the determined electrical delay and the measured electrical pacing impedance for each of the plurality of vectors; and
sort on the display screen the plurality of vectors based on the electrical delay.

13. The system of claim 11, wherein the controller is further configured to sort on the display screen the plurality of vectors based on the measured electrical impedance.

14. The system of claim 11, wherein the controller is further configured to determine a phrenic nerve stimulation threshold value for the first sub-set of the plurality of vectors.

15. The system of claim 14, wherein the controller is further configured to sort the vectors based, at least in part, on the phrenic nerve stimulation threshold.

16. The system of claim 11, further comprising:
a pulse generator configured to deliver electrical stimulation pulses to the patient's heart,
wherein the controller is configured to program the pulse generator to deliver electrical stimulation pulses to the patient's heart using the selected vector.

* * * * *